(12) United States Patent
McMaster

(10) Patent No.: US 10,119,208 B2
(45) Date of Patent: Nov. 6, 2018

(54) METHOD FOR MAKING ELECTRICALLY CONDUCTIVE TEXTILES AND TEXTILE SENSOR

(71) Applicant: FOOTFALLS AND HEARTBEATS LIMITED, Auckland (NZ)

(72) Inventor: Simon Adair McMaster, Grantham (GB)

(73) Assignee: FOOTFALLS AND HEARTBEATS LIMITED, Auckland (NZ)

( * ) Notice: Subject to any disclaimer, the term of this patent is extended or adjusted under 35 U.S.C. 154(b) by 179 days.

(21) Appl. No.: 14/912,351

(22) PCT Filed: Aug. 14, 2014

(86) PCT No.: PCT/IB2014/063929
§ 371 (c)(1),
(2) Date: Feb. 16, 2016

(87) PCT Pub. No.: WO2015/022671
PCT Pub. Date: Feb. 19, 2015

(65) Prior Publication Data
US 2016/0186366 A1    Jun. 30, 2016

Related U.S. Application Data

(60) Provisional application No. 61/866,576, filed on Aug. 16, 2013.

(51) Int. Cl.
*D04B 1/14* (2006.01)
*D04B 1/24* (2006.01)

(52) U.S. Cl.
CPC ............... *D04B 1/14* (2013.01); *D04B 1/24* (2013.01); *D10B 2403/02431* (2013.01)

(58) Field of Classification Search
CPC ..... D04B 1/14; D04B 1/24; D04B 1/22; D04B 1/243; D04B 1/246; D04B 1/26
See application file for complete search history.

(56) References Cited

U.S. PATENT DOCUMENTS 4,207,885 A    6/1980  Hampton et al.
4,715,235 A   12/1987  Fukui et al.
(Continued)

FOREIGN PATENT DOCUMENTS

DE        20209219 U1     8/2002
DE     102008003124 A1    7/2009
(Continued)

OTHER PUBLICATIONS

International Search Report in International Application No. PCT/IB2014/063929. dated Nov. 27, 2014.

*Primary Examiner* — Danny Worrell
(74) *Attorney, Agent, or Firm* — Venable LLP; Michele V. Frank

(57) ABSTRACT

A method for making a textile sensor and a textile sensor can include selecting a combination of variables from the group consisting of yarn variables, stitch variables, and textile variables; and knitting an electrically conductive yarn in the textile sensor in accordance with the selected combination of variables, wherein the combination of variables is selected so as to provide a controlled amount of contact resistance in the textile sensor. The method and textile can further include a capacitive textile-sensor having at least two integrally knit capacitor plate elements and having a configuration adapted for a sensing activity. Resistance in the textile sensor can automatically calibrate to a stable baseline level after the textile sensor is applied to a body.

15 Claims, 19 Drawing Sheets

(56) References Cited

U.S. PATENT DOCUMENTS

| | | | |
|---|---|---|---|
| 4,795,998 A | 1/1989 | Dunbar et al. | |
| 6,080,690 A | 6/2000 | Lebby et al. | |
| 6,145,551 A | 11/2000 | Jayaraman et al. | |
| 6,341,504 B1 * | 1/2002 | Istook | A61B 5/0002 2/69 |
| 6,543,299 B2 | 4/2003 | Taylor | |
| 6,970,731 B1 * | 11/2005 | Jayaraman | A61B 5/0008 600/388 |
| 7,144,830 B2 | 12/2006 | Hill et al. | |
| 7,161,084 B2 | 1/2007 | Sandbach | |
| 7,329,323 B2 | 2/2008 | Dhawan et al. | |
| 7,365,031 B2 | 4/2008 | Swallow et al. | |
| 7,377,133 B2 | 5/2008 | Sandbach et al. | |
| 7,544,627 B2 | 6/2009 | Tao et al. | |
| 7,559,902 B2 * | 7/2009 | Ting | A61B 5/0408 600/300 |
| 7,770,473 B2 | 8/2010 | Von Lilienfeld-Toal et al. | |
| 7,779,656 B2 | 8/2010 | Dias et al. | |
| 7,871,661 B2 * | 1/2011 | Maghribi | A61N 1/0551 427/171 |
| 7,878,030 B2 * | 2/2011 | Burr | D04B 1/14 66/173 |
| 8,034,001 B2 * | 10/2011 | Gal | A61B 5/1135 600/534 |
| 8,116,898 B2 | 2/2012 | Chung et al. | |
| 8,191,433 B2 | 6/2012 | Tao et al. | |
| 8,214,008 B2 | 7/2012 | Hassonjee et al. | |
| 8,298,968 B2 | 10/2012 | Swallow et al. | |
| 8,476,172 B2 | 7/2013 | Christof | |
| 8,669,195 B2 | 3/2014 | Swallow et al. | |
| 8,684,924 B2 * | 4/2014 | Ouwerkerk | A61B 5/16 600/301 |
| 8,925,392 B2 | 1/2015 | Esposito et al. | |
| 8,966,942 B2 * | 3/2015 | Dias | D04B 1/14 66/170 |
| 9,032,762 B2 * | 5/2015 | Begriche | D04B 1/22 66/171 |
| 9,435,058 B2 * | 9/2016 | Dias | D04B 1/14 |
| 2003/0186607 A1 * | 10/2003 | Goldberg | A61N 1/0408 442/304 |
| 2006/0258247 A1 | 11/2006 | Tao et al. | |
| 2006/0281382 A1 * | 12/2006 | Karayianni | D03D 1/0088 442/181 |
| 2007/0089800 A1 | 4/2007 | Sharma | |
| 2007/0298666 A1 * | 12/2007 | Kurth | D04B 1/16 442/1 |
| 2008/0307899 A1 | 12/2008 | Von Lilienfeld-Toal et al. | |
| 2009/0013728 A1 | 1/2009 | Dias et al. | |
| 2009/0018428 A1 | 1/2009 | Dias et al. | |
| 2011/0015498 A1 | 1/2011 | Mestrovic et al. | |
| 2011/0030127 A1 | 2/2011 | Dias et al. | |
| 2013/0192071 A1 | 8/2013 | Esposito et al. | |

FOREIGN PATENT DOCUMENTS

| | | |
|---|---|---|
| EP | 1916323 A2 | 4/2008 |
| JP | 2003-020538 A | 1/2003 |
| WO | 2004/100874 A2 | 11/2004 |
| WO | 2004100784 A2 | 11/2004 |
| WO | 2009/093040 A1 | 7/2009 |
| WO | 2012/101374 A1 | 8/2012 |
| WO | 2014/080404 A1 | 5/2014 |
| WO | 2014122619 A1 | 8/2014 |

* cited by examiner

| MER (kΩ.cm) | SJ | SP - A | SP - B | SP - C | SP - D |
|---|---|---|---|---|---|
| Course - relaxed | 0.129 | 0.022 | 0.017 | 0.011 | 0.020 |
| Course - tensioned | 0.041 | 0.009 | 0.004 | 0.003 | 0.004 |
| Wale - relaxed | 0.108 | 0.021 | 0.015 | 0.011 | 0.020 |
| Wale - tensioned | 0.035 | 0.009 | 0.003 | 0.002 | 0.003 |
| Course - Dynamic Range % | 68 | 59 | 76 | 73 | 80 |

FIB. 5B

| Temperature (°C) | Resistivity (KΩ) | |
|---|---|---|
| | Polyester | Merino Wool |
| 10 | 1.43 | 0.62 |
| 15 | 1.39 | 0.6 |
| 20 | 1.33 | 0.568 |
| 25 | 1.29 | 0.542 |
| 30 | 1.26 | 0.525 |
| 35 | 1.2 | 0.509 |
| 40 | 1.16 | 0.493 |

| Time (Seconds) | Diameter of "Calf" Tubes Tested | | | | |
|---|---|---|---|---|---|
| | 8.6 in. | 9.4 in. | 10.2 in. | 11 in. | 12.6 in. |
| | Resistance (Ohms) | | | | |
| 0 | 50.06 | 52.8 | 56.38 | 53.58 | 67.17 |
| 5 | 48.09 | 51.47 | 54.82 | 52.22 | 66.06 |
| 10 | 47.97 | 50.95 | 54.56 | 51.72 | 65.51 |
| 15 | 47.63 | 50.68 | 54.12 | 51.49 | 65.18 |
| 20 | 47.30 | 50.15 | 53.79 | 51.32 | 64.93 |
| 25 | 47.28 | 50.39 | 53.64 | 51.17 | 64.73 |
| 30 | 47.25 | 50.23 | 53.56 | 51.01 | 64.62 |
| 35 | 47.21 | 50.15 | 53.5 | 50.97 | 64.52 |
| 40 | 47.17 | 50.03 | 53.35 | 50.89 | 64.42 |
| 45 | 47.14 | 50.01 | 53.25 | 50.83 | 64.4 |
| 50 | 47.06 | 49.53 | 53.2 | 50.78 | 64.3 |
| 55 | 47.00 | 49.54 | 53.15 | 50.76 | 64.13 |
| 60 | 46.94 | 49.5 | 53.04 | 50.68 | 63.99 |
| 65 | 46.90 | 49.85 | 52.98 | 50.64 | 63.93 |
| 70 | 46.85 | 49.79 | 52.92 | 50.59 | 63.87 |
| 75 | 46.79 | 49.72 | 52.93 | 50.56 | 63.83 |
| 80 | 46.71 | 49.68 | 52.91 | 50.51 | 63.77 |
| 85 | 46.70 | 49.67 | 52.85 | 50.5 | 63.72 |
| 90 | 46.68 | 49.62 | 52.77 | 50.45 | 63.69 |
| 95 | 46.67 | 49.58 | 52.78 | 50.44 | 63.61 |
| 100 | 46.65 | 49.56 | 52.7 | 50.41 | 63.59 |
| 105 | 46.65 | 49.19 | 52.67 | 50.33 | 63.53 |
| 110 | 46.65 | 49.15 | 52.61 | 50.3 | 63.47 |
| 115 | 46.60 | 49.16 | 52.58 | 50.28 | 63.38 |
| 120 | 46.57 | 49.11 | 52.53 | 50.28 | 63.32 |
| Mean | 47.14 | 49.98 | 53.34 | 50.91 | 64.30 |
| Std. Dev. | 0.72 | 0.80 | 0.85 | 0.72 | 0.89 |
| 95% CI | 0.28 | 0.31 | 0.33 | 0.28 | 0.35 |
| CI Limits | 46.86-47.42 | 49.67-50.29 | 53.01-53.67 | 50.63-51.19 | 63.95-64.65 |

FIG. 23

| Time | Diameter of "Ankle" Tubes Tested | | | | |
|---|---|---|---|---|---|
| (Seconds) | 8.6 in. | 9.4 in. | 10.2 in. | 11 in. | 12.6 in. |
| | Resistance (Ohms) | | | | |
| 0 | 43.01 | 51.71 | 28.91 | 58.46 | 95.56 |
| 5 | 42.58 | 49.01 | 28.00 | 57.31 | 94.47 |
| 10 | 41.83 | 48.59 | 27.71 | 56.65 | 93.94 |
| 15 | 41.73 | 48.14 | 27.47 | 56.29 | 93.71 |
| 20 | 41.41 | 47.43 | 27.29 | 56.03 | 93.39 |
| 25 | 41.42 | 47.90 | 27.34 | 55.94 | 93.19 |
| 30 | 41.33 | 48.18 | 27.39 | 55.80 | 93.06 |
| 35 | 41.31 | 48.43 | 27.54 | 55.65 | 92.93 |
| 40 | 41.27 | 47.85 | 27.46 | 55.52 | 92.80 |
| 45 | 41.19 | 47.78 | 27.37 | 55.41 | 92.69 |
| 50 | 41.11 | 47.76 | 27.51 | 55.38 | 92.66 |
| 55 | 41.11 | 49.06 | 27.21 | 55.28 | 92.57 |
| 60 | 41.11 | 48.62 | 26.74 | 55.21 | 92.54 |
| 65 | 41.03 | 48.42 | 27.07 | 55.16 | 92.53 |
| 70 | 41.10 | 47.69 | 26.76 | 55.19 | 92.43 |
| 75 | 40.95 | 47.80 | 26.68 | 55.08 | 92.37 |
| 80 | 40.92 | 47.64 | 26.81 | 55.13 | 92.30 |
| 85 | 40.89 | 47.68 | 26.86 | 55.11 | 92.30 |
| 90 | 40.86 | 47.48 | 27.21 | 55.01 | 92.14 |
| 95 | 40.82 | 47.52 | 26.71 | 54.98 | 92.09 |
| 100 | 40.83 | 47.53 | 26.78 | 54.89 | 92.05 |
| 105 | 40.85 | 47.66 | 26.59 | 54.82 | 92.06 |
| 110 | 40.86 | 47.30 | 26.55 | 54.77 | 91.93 |
| 115 | 40.88 | 47.55 | 26.67 | 54.78 | 91.89 |
| 120 | 40.86 | 47.35 | 26.69 | 54.70 | 91.82 |
| Mean | 41.25 | 48.08 | 27.17 | 55.54 | 92.78 |
| Std. Dev. | 0.53 | 0.88 | 0.52 | 0.85 | 0.86 |
| 95% CI | 0.21 | 0.34 | 0.20 | 0.33 | 0.34 |
| CI Limits | 41.04-41.46 | 47.74-48.42 | 26.97-27.37 | 55.21-55.87 | 92.44-93.12 |

FIG. 26

METHOD FOR MAKING ELECTRICALLY CONDUCTIVE TEXTILES AND TEXTILE SENSOR

FIELD OF INVENTION

The present invention relates to a method for optimizing contact resistance in electrically conductive yarns and textiles, and textiles having such optimized contact resistance. Contact resistance can be optimized for particular desired uses of a yarn or textile product by adjusting physical, chemical, and/or mechanical variables in accordance with parameters predictable for such uses.

BACKGROUND

Constructing electrical circuits in textile materials presents a number of challenges. Conventional electrical circuits in textiles include conductive fibers knit or woven into a fabric, and capacitance or bioelectric sensors, transducers, or the like inserted into a textile structure. Such efforts have disadvantages, such as conductive fabrics that cannot be worn against a wearer's skin or must be limited to a small surface area. In garments having a sensor added to a fabric, design processes become complicated and manufacturing costs are increased.

An increasingly important field in textiles is that of "intelligent textiles" in which electrical signals representing physiological data are collected from garments and transmitted to remote locations, for example, for monitoring, assessment, and intervention by health care professionals. However, such textile devices are generally not truly "intelligent" textiles, as they comprise solid-state electronics placed in a textile shell and worn as apparel.

Previous efforts have been made to provide such "intelligent textiles." For example, one attempt includes a deformation-sensitive knitted or woven fabric structure of intertwined yarns having an electrical resistance that varies with degree of deformation. Another attempt to enhance electrical transmissions comprises a sensor array constructed from conductive threads in which the thread contacts are made with piezo-resistive junctions such that contact resistance changes with applied pressure. Another fabric includes a pressure-activated electrical sensor integrated into a knitted fabric such that fiber contact resistance can be related to compression force. Another knitted fabric that is designed to sense pressure and strain utilizes a single conductive yarn type, in which the applied pressure or strain causes different contact areas and resistances between adjacent loops of the yarn. In yet another example, a knitted electronic transducer utilizes a combination of conductive and non-conductive yarns such that extension in the course or wale direction causes loops in the transducer to separate or come together, varying the electrical resistance of the article. However, none of these efforts has addressed the optimal construction of a textile for suitably overcoming the challenges of contact resistance in such a device.

Thus, there is a need for a method for designing a textile structure to control the position and size of yarn contact areas for controlling electrical contact resistance and sensitivity of the structure to deformation. There is a need for such a method that utilizes a predictable stitch structure that improves control of contact resistance. There is a need for such a method that provides a means for varying a textile structure for specific applications. There is a need for such a method that allows use of a single conductive fiber type in a textile sensor. There is a need for such a method that allows the textile structure to be utilized as a sensor for force, pressure, movement or temperature.

SUMMARY OF THE INVENTION

Embodiments of a method for optimizing contact resistance in electrically conductive yarns and textiles, and textiles having such optimized contact resistance, of the present invention can comprise selecting a sensing activity for the textile; selecting a combination of variables from the group consisting of yarn variables, stitch variables, and textile variables; and knitting an electrically conductive yarn in the textile in accordance with the selected combination of variables, wherein the knitted combination of variables provides an optimal contact resistance in the textile correlated with a desired electrical conductivity for the sensing activity. In some embodiments, the knitted combination of variables provides a predictable yarn contact area for the electrically conductive yarn correlated with the optimal contact resistance.

Other embodiments of a method for optimizing contact resistance in electrically conductive yarns and textiles, and textiles having such optimized contact resistance, can comprise selecting a combination of variables from the group consisting of yarn variables, stitch variables, and textile variables; and knitting an electrically conductive yarn having a yarn contact area in the textile in accordance with the selected combination of variables, wherein the knitted combination of variables provides a controllable amount of contact resistance in the textile. Some embodiments can further include selecting a sensing activity for the textile, and a controlled amount of contact resistance in the textile is correlated with a desired electrical conductivity for the sensing activity.

Some embodiments can further include selecting a measurement sensitivity for the sensing activity, and the knitted combination of variables can provide the optimal contact resistance in the textile correlated with a desired electrical conductivity for the measurement sensitivity. In various embodiments, the sensing activity can be selected from sensing tensile force, compressive force, movement, temperature, and physiological activity.

Some embodiments of a textile according to the present invention can comprise a sensing area comprising an electrically conductive yarn knitted in the textile and adapted for a sensing activity; and the sensing area comprising a combination of variables selected from the group consisting of yarn variables, stitch variables, and textile variables, wherein the combination of variables provides an optimal contact resistance in the textile correlated with a desired electrical conductivity for the sensing activity. In some embodiments, the combination of variables can comprise a predictable yarn contact area for the electrically conductive yarn correlated with the optimal contact resistance.

Some embodiments of a textile according to the present invention can comprise a sensing area comprising an electrically conductive yarn knitted in the textile; and the sensing area comprising a combination of variables selected from the group consisting of yarn variables, stitch variables, and textile variables, wherein the combination of variables provides a controllable amount of contact resistance in the textile. In such an embodiment, the sensing area can be adapted for a sensing activity, and a controlled amount of contact resistance in the textile can be correlated with a desired electrical conductivity for the sensing activity.

The combination of variables can be selected from yarn variables, including yarn type, yarn fabrication method, and yarn count; stitch variables including stitch pattern, stitch length, and stitch percentage; and textile variables including electrical resistivity, fabric thickness, fabric weight, optical porosity, and percentage permanent stretch.

Some embodiments of a textile according to the present invention can comprise a method for making a textile sensor, comprising selecting a combination of variables from the group consisting of yarn variables, stitch variables, and textile variables; and knitting an electrically conductive yarn in the textile sensor in accordance with the selected combination of variables, wherein the combination of variables is selected so as to provide a controlled amount of contact resistance in the textile sensor. Some embodiments of a textile according to the present invention can comprise a textile sensor, comprising an electrically conductive yarn knitted in the textile sensor in accordance with a combination of variables selected from the group consisting of yarn variables, stitch variables, and textile variables, wherein the combination of variables is selected so as to provide a controlled amount of contact resistance in the textile sensor.

In some such embodiments, the selected combination of variables can further comprise an increased tex yarn count so as to provide an increased cover factor and a decreased amount of contact resistance. In some such embodiments, the selected combination of variables can further comprise a filament yarn so as to provide an increased amount of contact resistance, whereby the textile sensor is adapted to have decreased measurement sensitivity for measuring large mass or pressure differences. In some such embodiments, the selected combination of variables can further comprise a staple fiber yarn so as to provide a decreased amount of contact resistance, whereby the textile sensor is adapted to have increased measurement sensitivity for measuring small mass or pressure differences.

Some such embodiments can further comprise a capacitive textile-sensor having at least two integrally knit capacitor plate elements comprising the electrically conductive yarn and having a configuration adapted for a sensing activity. In such a capacitive textile-sensor, the configuration can further comprise a selected contact resistance within the knitted capacitor plate elements. In such a capacitive textile-sensor, the capacitor plate elements can each further comprise a defined yarn contact area, and the selected contact resistance can comprise a selected number and shape of yarn contact points within each yarn contact area. In such a capacitive textile-sensor, the configuration can further comprise a selected size, shape, and position of the capacitor plate elements and a diaelectric material within the capacitive textile-sensor. In such a capacitive textile-sensor, a measure of capacitance by the capacitive textile-sensor can correlate with an amount of strain in the capacitive textile-sensor. In such a capacitive textile-sensor, the capacitor plate elements can be knit as a series of spaced apart, interdigitated fingers. In such a capacitive textile-sensor, the capacitor plate elements can be knit into a defined area of two opposable fabric layers. In such a capacitive textile-sensor, the capacitive textile-sensor can be knit in a wearable garment during fabrication of the garment.

In some embodiments of a textile sensor according to the present invention, resistance in the textile sensor can automatically calibrate to a stable baseline level after the textile sensor is applied to a body. In some embodiments, resistance in the textile sensor can automatically calibrate to a stable baseline level within 90 seconds after the textile sensor is applied to a person's leg. In some embodiments, resistance in the textile sensor can automatically calibrate to a stable baseline level between 20-85 seconds after the textile sensor is applied to a person's calf or ankle.

Features of a method for optimizing contact resistance in electrically conductive yarns and textiles and products having such optimized contact resistance of the present invention may be accomplished singularly, or in combination, in one or more of the embodiments of the present invention. As will be realized by those of skill in the art, many different embodiments of a method for optimizing contact resistance in electrically conductive yarns and textiles and products having such optimized contact resistance according to the present invention are possible. Additional uses, advantages, and features of the invention are set forth in the illustrative embodiments discussed in the detailed description herein and will become more apparent to those skilled in the art upon examination of the following.

BRIEF DESCRIPTION OF THE DRAWINGS

FIG. 5B is a graph showing variations in fabric thickness relative to mean electrical resistivity in courses and in wales for the single jersey stitch pattern control and the four stitch patterns having different percentages of miss and tuck stitches in FIG. 2.

FIG. 23 is a table showing the results of measurements of resistance for a textile-sensor on five diameters of a tube simulating the calf of a person's leg in five second increments after the textile-sensor is applied, in an embodiment of the present invention.

FIG. 26 a table showing the results of measurements of resistance for a textile-sensor on five diameters of a tube simulating the ankle of a person's leg in five second increments after the textile-sensor is applied, in an embodiment of the present invention.

DETAILED DESCRIPTION

Figures 1, 2:
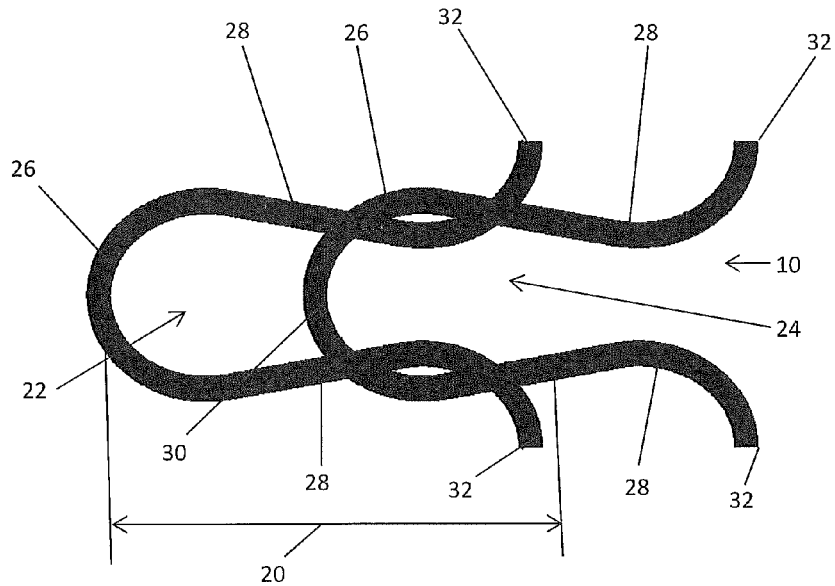
FIG. 1 is a diagrammatic view of two interconnected yarn units in a single jersey knit stitch pattern.
FIG. 2 is a table showing mean electrical resistivity (MER) values in a single jersey stitch pattern control and in four sample stitch patterns having different percentages of miss and tuck stitches. MER is shown for each stitch pattern having either relaxed or tensioned courses or relaxed or tensioned wales.

For the purposes of this description, unless otherwise indicated, all numbers expressing quantities, conditions, and so forth used in the description are to be understood as being modified in all instances by the term "about." Accordingly, unless indicated to the contrary, the numerical parameters set forth in the following description are approximations that can vary depending upon the desired properties sought to be obtained by the embodiments described herein. At the very least, and not as an attempt to limit the application of the doctrine of equivalents to the scope of the invention, each numerical parameter should at least be construed in light of the number of reported significant digits and by applying ordinary rounding techniques.

Notwithstanding that the numerical ranges and parameters setting forth the broad scope of the described embodiments are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a stated range of "1 to 10" should be considered to include any and all sub-ranges between (and inclusive of) the minimum value of 1 and the maximum value of 10, that is, all sub-ranges beginning with a minimum value of 1 or more, and ending with a maximum value of 10 or less.

As used in this description, the singular forms "a," "an," and "the" include plural referents unless the context clearly dictates otherwise. Thus, for example, the term "a yarn" is intended to mean a single yarn or more than one yarn. For the purposes of this specification, terms such as "forward," "rearward," "front," "back," "right," "left," "upwardly," "downwardly," and the like are words of convenience and are not to be construed as limiting terms. Additionally, any reference referred to as being "incorporated herein" is to be understood as being incorporated in its entirety.

The following definitions are for purposes of the description herein:

"Contact Resistance": The equation $$R_c = \frac{\rho}{2}\sqrt{\frac{\pi H}{F}}$$

is a representation of the Holm contact resistance equation, where $R_c$ is contact resistance, $\rho$ is material resistivity, H is material hardness, and F is the normal force. The equation $$R_c = \frac{\rho}{2}\sqrt{\frac{\pi H}{nP}}$$

is another representation of the Holm equation, which is more relevant to textile based contact resistance. F is replaced by nP, where n is the number of contact points, and P is the contact pressure. Material hardness and electrical resistivity are constants that depend on the material properties of a textile. Contact resistance is therefore inversely proportional to the number of contact points and the contact pressure. That is, more contact points result in lower contact resistance. Therefore, as the number of contact points and/or contact pressure increases, contact resistance decreases. As used herein, contact resistance provides a measure of electrical conductivity in a yarn or textile. At the "micro" scale, surface roughness limits surface-to-surface contact. In addition, as pressure increases, the number of contact points increases, and eventually at the "nano" scale individual contact points "combine" into a larger contact area. "Integration as Summation" and the "Finite Element Method (FEM)" are techniques that can be used to determine the limits of these contacts points and therefore the contact area they produce.

"Course" is defined as a horizontal row of interlooped stitches running across the width of a knitted fabric.

"Force" is defined as any influence that causes an object to undergo a certain change, either concerning its movement, direction, or geometrical shape. In relation to a flexible textile network, force may be manifested as tension, compression, or movement of the fabric structure.

"Miss stitch" is defined as a knitting stitch in which at least one needle holds the old loop and does not receive any new yarn across one or more wales. A miss stitch connects two loops of the same course that are not in adjacent wales.

"Plain stitch" is defined as a knitting stitch in which a yarn loop is pulled to the technical back of a fabric. A plain stitch produces a series of wales or lengthwise ribs on the face of the fabric and courses, or cross-wise loops, on the back. A plain stitch can also be referred to as a "single-knit jersey stitch" or a "single jersey stitch."

"Tuck stitch" is defined as a knitting stitch in which a yarn is held in the hook of a needle and does not form a new loop.

"Wale" is defined as a vertical row of interlooped stitches formed by the action of one needle in successive courses along the length of a fabric.

Certain other definitions are provided elsewhere in this description.

The present invention can include embodiments of a method, or process, for optimizing contact resistance in electrically conductive yarns and textiles, and textiles, or textile products, having such optimized contact resistance. FIGS. 1-20 illustrate such embodiments. Contact resistance can be optimized for particular desired uses of a yarn or textile product by adjusting physical, chemical, and/or mechanical variables in accordance with parameters desired for such uses. An exemplary embodiment can comprise a method for designing and/or constructing a textile structure by controlling stitch pattern, percentage of different stitches within the stitch pattern, stitch density, yarn composition, yarn fabrication method, and/or yarn size.

Controlling such variables can control the number, location, and size (that is, quality) of yarn contact points (yarn contact area 52), and thus optimize the contact resistance and sensitivity of the textile structure for a particular type of measurement. The ability to control and adjust contact resistance for optimal sensor-specific electrical conductivity is due, at least in part, to the proportional relationships between stitch, yarn, and textile variables, or characteristics, and yarn contact area (52). For example, contact resistance can be controlled by inserting and removing various stitch types as a percentage of an overall knit structure so as to alter the size and shape of the yarn contact area (52). Such a method can take into account the three-dimensional complexity of a textile structure, including, for example, interactions of fibers within the yarn itself, and the relationship of controllable variables to electrical resistance characteristics during deformation of the textile structure.

In addition, selection and control of such stitch, yarn/fiber, and textile variables for providing optimal contact resistance for a particular use of a textile structure can be predictable, for example, a mathematically predictable selection of variables and correlated contact resistance.

In some embodiments, such a method for optimizing contact resistance can be applied to flexible electrically conductive yarns, textiles, and products. In some embodiments, knitted yarns can function as an electrically conductive sensor or network of sensors. Such a knit structure can be manufactured in such a way that it can be used to make a close-fitting and comfortable garment. The garment can be, for example, a compression garment, or a garment that acts in manner similar to a compression garment. In some embodiments, the textile structure can be formed within a conventional garment and utilized as a sensor. That is, the textile structure can have fully integrated knitted sensors, rather than electronic components inserted into fabrics as in conventional textiles. As a result, the textile structure can be customized so that sensors can be placed at various desired locations in the textile structure. Such sensors can be utilized to measure force, pressure, strain, movement, temperature, physiological activity, and/or other variables.

In some embodiments, a method for optimizing contact resistance of the present invention can be applied to electrically conductive yarns, textiles, and textile products that are flexible. Control of contact resistance in a flexible network of electrically conductive yarn allows the textile structure itself to act as a sensing element. That is, "the textile is the sensor." In such an embodiment, no additional mechanical or solid-state electrical components are needed for the textile to measure desired variables. Some embodiments of a textile product having optimized contact resistance can be interchangeably described as "textile-as-sensor" or "textile-sensor."

Such a flexible textile-sensor in accordance with the present invention has a number of advantages. For example, one advantage is that as a result of the ability to control and optimize contact resistance, such a textile-sensor can effectively function in a variety of sensing applications. Another advantage of the ability to control and optimize contact resistance is that in a textile designed to perform a sensing function, conductivity can be enhanced for the type of signal being sensed so as to provide more accurate sensing and signal transmission. Another advantage of such a textile-sensor is that the shape of the sensor, or sensing area, can be controlled. The geometric shape of a sensor can affect how it functions. For example, in a textile-sensor utilized for sensing respiratory rate, a sensor, or sensing area, having the shape of a sine wave provides a clearer signal and uses less power than sensors having other shapes. In addition, the type and shape of sensor can affect how sensing activity interfaces with electronics for signal measurement, transmission, and/or recording associated with the textile-sensor. Accordingly, differently shaped sensors in a textile-sensor can be advantageously utilized for different applications.

Another advantage of controlling electrical signals solely in a textile structure itself is that contact resistance can be optimized on macro scale ($>2.5\times10^{-3}$ m$^2$) and on a nano scale. Another advantage of the ability to control and optimize contact resistance in the textile structure itself is that the textile-sensor can be customized to include any number of sensing areas. For example, such a textile-sensor can include a single, large sensing area or a plurality of smaller sensing areas. In certain embodiments, the textile-sensor capability can be combined with other fiber/yarn material characteristics to provide even further sensing functionality.

Another advantage of embodiments of such a textile-sensor is that the sensing structure can comprise a single layer of fabric. In contrast, conventional sensors, such as capacitive type sensors, can require multiple layers of fabric and fixed plates to function. Embodiments of such a textile-sensor can comprise a resistive sensor network that allows multiple types of sensing without the addition of fabric layers. As a result, some embodiments of such a textile-sensor can comprise a form-fitting, customizable garment that can be readily worn against the skin and thus allow a wide range of applications. For example, some embodiments of such a resistive textile-sensors placed against a wearer's skin can sense force changes in the wearer, such as respiration rate, mechanical joint movement, or strain during exercise. In certain embodiments, such resistive textile-sensors can perform physiological sensing, for example, sensing a heart rate signal, brain wave signal, or other muscle activity.

Some embodiments of a textile structure of the present invention provide advantages in comfort over conventional textile-based sensors. For example, conventional textile-based sensors may be limited to woven and/or layered structures, which limit the number of materials suitable for use and/or prevent close skin contact without chafing. Existing sensors that require multiple layers of fabric and fixed plates to function also constrain comfort and wearability of a textile sensing device. Thus, another advantage of such a textile-sensor of the present invention is that without additional mechanical and/or electrical components or additional layers of fabric, a knitted textile-sensor can provide greater comfort and durability in a wearable product.

In embodiments of a method according to the present invention, optimizing contact resistance in electrically conductive yarns and textiles can comprise controlling and/or optimizing yarn variables, stitch variables, and/or textile variables so as to control and/or optimize yarn contact area (52).

Physical yarn variables, or yarn characteristics, that can affect contact resistance include, for example: (1) yarn type or composition; (2) yarn fabrication method; and (3) yarn count.

Yarn type, or composition, influences yarn surface topography (surface roughness), and thus yarn contact area (52), in an electrically conductive yarn and/or textile. For purposes of this description, yarn type, or composition, includes characteristics such as whether a yarn is natural or synthetic, a staple fiber spun yarn, a filament yarn, single or multifilament, single or multi-ply, type and degree of twist, whether the yarn is textured, and/or other characteristics. Likewise, the method by which a yarn is fabricated, such as yarn spinning method, affects how the yarn influences yarn surface topography and yarn contact area (52).

Accordingly, yarn type, or composition, and yarn fabrication method affect contact resistance in a knitted fabric. Various electrically conductive fibers and yarns can be used to construct a textile structure having optimized contact resistance according to the present invention. For example, some embodiments of such a textile structure can be constructed using an electrically conductive silver yarn, or silver-coated yarn, an electrically conductive polyester-stainless steel yarn, or a combination of such yarns. Different types of yarn and different methods by which a yarn is made can affect yarn contact area (52) and contact resistance differently. Contact resistance-optimized textile structures comprising selected electrically conductive yarn types, compositions, and fabrication methods can be utilized in various applications to measure pressure, movement, and/or temperature.

Yarn count refers to the linear mass density of fibers and is defined as the mass in grams per 1000 meters, expressed as "tex." That is, yarn count is a measure of the size of a yarn. Yarn count correlates to yarn diameter and therefore yarn contact area (52). In particular, a yarn having a higher yarn count can provide a larger yarn contact area (52) and thus lower contact resistance.

"Cover factor" is defined as the ratio of fabric surface occupied by yarns to total fabric surface. Cover factor is related to yarn count, or density, and can be represented by the calculation: Cover factor $(CF)=\sqrt{tex}/loop$ length (l). Accordingly, tex is directly related to cover factor and inversely related to contact resistance. That is, an increase in tex of a yarn (in similar gauge needles) results in an increase in cover factor, which correlates with a decrease in contact resistance. Conversely, a decrease in tex of a yarn (in similar gauge needles) results in a decrease in cover factor and an increase in contact resistance.

Staple fiber yarns (typically about 25-35 mm in length) intrinsically have more yarn contact points (42, 44, 46, 48, 50) and therefore more yarn contact area (52) than filament yarns (depending in part on the type of conductive yarn). Thus, staple fiber yarns (having a greater density) provide a larger cover factor and a relatively lower contact resistance than filament yarns.

Figure 3A:
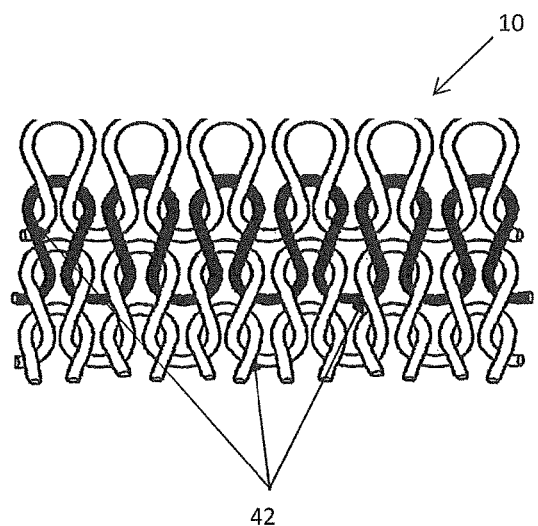
FIG. 3A is a diagrammatic view of a plain single jersey knit stitch pattern.
Figure 3B:
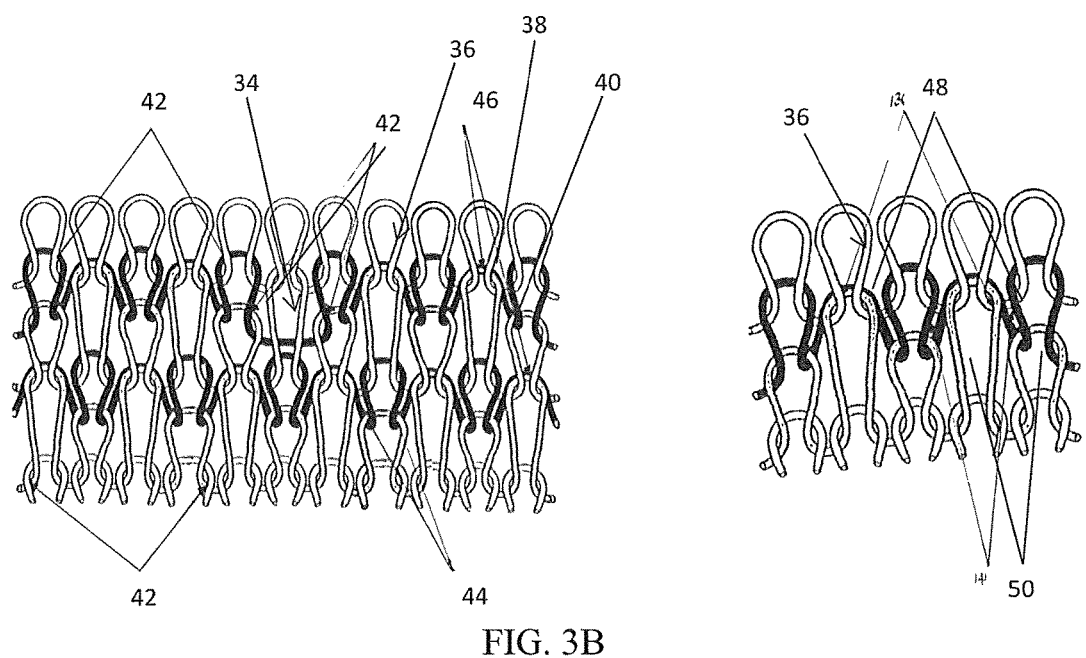
FIG. 3B is a diagrammatic view of a knit stitch pattern having single jersey stitches, miss stitches, and tuck stitches and showing yarn contact points in a tuck stitch in an embodiment of the invention.
Figure 4:
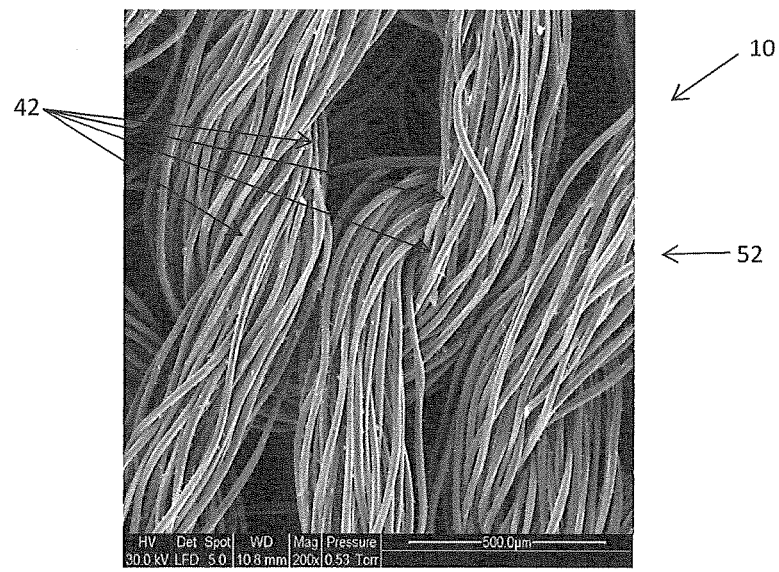
FIG. 4 is a scanning electron microscope image of the yarn contact area for a single jersey, weft knitted fabric coated with polypyrrole (Ppy) conducting polymer in an embodiment of the invention.

Stitch variables, or characteristics, that can affect contact resistance include, for example: (1) stitch type, composition, or pattern; (2) stitch length; and (3) stitch percentage. Stitch type, composition, or pattern influence yarn contact area (52), as shown in FIGS. 3 and 4. One common stitch type, shown in FIG. 3A, is a plain, single jersey stitch pattern 10. The single jersey stitch pattern 10 has interconnecting stitch loops 22, 24 that touch at single jersey contact points 42. Another stitch type useful in embodiments of the present invention is a "purl" stitch. A purl stitch pattern comprises all loops in one or more courses knit from face to back, and all loops in the next one or more courses knit from back to face. The stitch type, composition, or pattern determines the configuration of the yarn in a textile, which influences the yarn contact area (52) and thus contact resistance.

Stitch length 20 is defined as a length of yarn which includes the needle loop 22 and half of the sinker loop 24 on either side of it. Generally, the longer the stitch length 20, the more extensible and lighter the fabric, and the greater the potential number of yarn contact points (for example, 42, 44, 46, 48, 50). As shown in FIG. 3B, stitch length 20 and stitch composition have been altered from that shown in FIG. 3A, resulting in an increased number of contact points 42, 44, 46, 48, 50. Three stitches in a particular pattern provide an increased number of yarn contact points compared to the number of contact points provided by two stitches, which in turn provide an increased number of yarn contact points compared to the number of contact points provided by one stitch. Accordingly, stitch length 21 influences the yarn contact area 52 and thus contact resistance.

Stitch Percentage is defined as the percentage of stitch type in a stitch pattern. For example, stitch percentage can refer to the percentage of single jersey, miss, or tuck stitches 10, 34, 36, respectively, in a stitch pattern, or the percentage of purl stitches in a different stitch pattern. Stitch percentage relates to fabric thickness. A stitch percentage that increases fabric thickness results in a larger yarn contact area (52), and therefore a corresponding decrease in contact resistance (and an increase in electrical conductivity). A stitch percentage variable, or metric, relates to a fabric/sensor at rest. When a force is applied, a fabric generally decreases in thickness.

Yarn contact area (52) has a direct influence on contact resistance of a textile structure. Contact resistance is associated with the conduction characteristic of the yarn contact surface area (52). The larger the yarn contact area (52) and the less the surface roughness of the yarn surface, the better the conductivity. An increase in yarn contact area (52) causes a proportional decrease in contact resistance. Yarn variables, stitch variables, and textile variables each influence yarn contact area (52), and thereby provide variables that can be used to control and/or optimize yarn contact area (52) and thus contact resistance and yarn conductivity.

Yarn contact area is illustrated in FIGS. 1, 3A, and 3B. FIG. 1 is a schematic representation of a single jersey stitch 10. In a single jersey knit fabric, a needle loop 22, or yarn unit, comprises a head 26 and two side legs 28 that form a noose 30. At the base of each leg 28 is a foot 32, which meshes through the head 26 of the loop 24 formed at the previous knitting cycle. The leg 28 of the needle loop 22 passes from one side (or face) to the other side/face of the sinker loop 24 across the leg 28 and head 26 of the sinker loop 24, and then loops around to pass back across the head 26 and opposite leg 28 of the sinker loop 24 to back to the original side/face of the sinker loop 24.

FIGS. 3A and 3B are schematic representations of stitch structures showing points of yarn contact. FIG. 3A is a schematic drawing of a single jersey stitch pattern. As shown in FIG. 3A, interconnecting stitch loops touch at single jersey contact points 100. In a single jersey stitch pattern, one stitch contacts an adjacent stitch essentially on only one side, or surface, of the adjacent stitch (or fabric) at a time. That is, in two interconnected stitch loops, the legs of a first stitch loop contact the feet of a second, adjacent stitch loop on one surface of the second stitch loop. On the opposite surface of the second stitch loop, the head of the first stitch loop contacts the legs of the second stitch loop. As a result, single jersey contact points are limited to relatively small crossover points of adjacent loops.

FIG. 3B is a schematic drawing of a single jersey stitch pattern having miss and tuck stitches. A single jersey stitch pattern having miss and tuck stitches includes single jersey contact points 100, as well as additional contact points at the miss and tuck stitches.

A tuck stitch contact point 110 occurs when a tuck stitch loop interconnects in a course with adjoining stitch types. As shown in FIG. 3B, in a tuck stitch, the leg of the stitch loop passes around the head of an adjacent stitch loop. The leg of the tuck stitch loop contacts a first surface on one side of the head of an adjacent stitch loop. The leg of the tuck stitch loop then passes underneath to thereby contact a second surface of the head of the adjacent stitch loop at an angle substantially perpendicular to the first contact surface. Finally, the leg of the tuck stitch loop passes to the opposite side of the adjacent stitch loop so as to contact a third surface of the head of the adjacent stitch loop substantially perpendicular to the first contact surface and substantially parallel to the first contact surface.

It is understood that the contact(s) between the leg of the tuck stitch loop and the first, second, and third contact surfaces of the head of the adjacent stitch loop together form a continuous tuck stitch contact point (110) around the shape of the head of the adjacent stitch loop. As a result of this continuous contact configuration, the tuck stitch contact point 110 is approximately three times the size of the single jersey contact point 100. Due to the increased yarn contact area, the tuck stitch contact point 110 decreases contact resistance, as compared to the single jersey contact point 100.

A tuck loop contact point 120 occurs when the tuck loop of a tuck stitch presses upon the held loop of a tuck stitch. As shown in FIG. 3B, the head of the tuck loop contacts the head of the held loop along substantially the entire length of the heads of both the tuck loop and held loop. As a result, the yarn contact area (YCA) at the tuck loop contact point 120 is approximately one third the length of a tuck stitch loop length. Due to the increased yarn contact area, the tuck loop contact point 120 decreases contact resistance, as compared to the single jersey contact point 100. The tuck loop contact point 120 decreases yarn contact resistance when a textile incorporating tuck stitches is in a relaxed state or in a tensioned state.

A held loop contact point 130 is formed when the held loop of a tuck stitch is forced against an adjacent stitch loop. As shown in FIG. 3B, the head of the held loop of a tuck stitch contacts the foot of the adjacent stitch loop at the same point as the head of the tuck loop. The held loop contact point 130 has a similar size to the single jersey contact point 100, but provides a greater decrease in yarn contact resistance than the single jersey contact point 100 due to intrinsic stretch and recovery of a textile incorporating tuck stitches.

A tensioned tuck stitch contact point 140 is formed when a textile comprising tuck stitches is placed under tension. As shown in FIG. 3B, when the tuck stitch structure is placed under tension, the leg of the tuck stitch loop is forced into contact with the leg of an adjacent stitch loop. The yarn contact area of the tensioned tuck stitch contact point 140 is approximately one third the length of a stitch loop length. Due to the increased yarn contact area, the tensioned tuck stitch contact point 140 decreases contact resistance. The tensioned tuck stitch contact point 140 has a greater effect on yarn contact resistance when a textile incorporating such stitches is under tension.

As compared to the plain single jersey stitch pattern in FIG. 3A, the additional contact points 110, 120, 130, and 140 shown in the tuck stitch structures in FIG. 3B provide an increased number and quality of contact points. The quality of yarn contact points relates to factors such as the size of the surface area in contact between two or more portions of the yarn and the degree to which the contact points remain in contact as the textile, yarn, and stitches move during tensioning or deformation and relaxation. Accordingly, the tuck stitch contact points 110, 120, 130, and 140 provide increased yarn contact area and decreased contact resistance. Thus, embodiments of a method for optimizing contact resistance in electrically conductive yarns and textiles can comprise knitting tuck stitches. Likewise, textiles having such optimized contact resistance can comprise tuck stitches. Optimizing, and thus controlling, contact resistance in electrically conductive yarns and textiles by varying the number and quality of tuck stitch contact points can be applied to various forms of knitted textiles in which such stitches are utilized.

FIG. 4 is a scanning electron microscope image of the yarn contact area 52 for a single jersey 10, weft knitted fabric coated with polypyrrole (PPy) conducting polymer. FIG. 4 shows the extent of yarn contact points 42 in this single jersey 10 fabric sample. When a conductive knitted fabric is subject to a load, the yarn contact area 52 increases due to suppression of any fabric surface roughness and compression of individual monofilaments into a large conductive fiber. Yarn contact area 52 increases in proportion to the total yarn circumference in contact and the total number of fibers involved.

As described herein, yarn type or composition and yarn fabrication method each influence yarn surface topography, or surface roughness, and thus the size and shape, or configuration, of a yarn contact area (52). Likewise, stitch type, composition, or pattern, stitch length, and stitch percentage each influence yarn contact area (52). Accordingly, these variables affect contact resistance between adjacent yarns in a knitted fabric. Different electrically conductive yarns have a different configuration of yarn contact points. For example, an electrically conductive polyester-stainless steel yarn has a first configuration (size and shape) of yarn contact points. An electrically conductive silver-coated yarn has a second configuration (size and shape) of yarn contact points different from the first yarn contact point configuration of the polyester-stainless steel yarn. However, embodiments of methods for optimizing contact resistance according to the present invention have the advantage of applying generally to the surface topography of all yarns. That is, the predictability of a particular selection of yarn and stitch variables to optimize contact resistance for certain applications can apply in general to any electrically conductive yarn.

In embodiments of a method according to the present invention, physical textile variables that can be controlled and/or measured in relation to optimizing contact resistance include: (1) mean electrical resistivity (MER); (2) fabric thickness; (3) fabric weight; (4) optical porosity (OP); and (5) percentage permanent stretch (PPS).

Electrical resistivity of electrically conductive fabrics is conventionally measured primarily using a four-point probe system, with the results produced in ohms/square. This method is primarily used to measure thin film or sheet resistance, and assumes that the thin film is two-dimensional, whereby resistance is calculated using the equation $R=R_s(l/w)$, where $R_s$ is surface resistivity. Because textiles are three-dimensional, the depth dimension, although small relative to width and length, provides the basis for further contact points within a sensor structure. Therefore, for purposes herein, surface resistivity is measured in ohms and volume resistivity in ohms-cm ($\Omega$-cm), or ohms.cm ($\Omega$.cm). Using a two-probe method, as described herein, allows for monitoring electrical signal output in both horizontal and vertical directions (measured in ohms-cm). Such a two-probe method can further allow monitoring of signal output through increments of 360° if probes are thusly attached on the sensor.

Mean Electrical Resistance (MER) (k$\Omega$-cm) is defined as the measurement of the output that registers resistance in a fabric. MER in a textile can range from about 20±1 $\Omega$.-cm to about 500±15 k$\Omega$.-cm. MER measured in the course direction is different from MER measured in the wale direction. In embodiments of the present invention, optimizing contact resistance optimizes
mean electrical resistivity (MER). That is, as yarn contact area (52) increases, yarn contact resistance decreases, and MER decreases.

Fabric thickness (mm) impacts the ability to optimize conductivity in a fabric. As demonstrated in FIG. 5B, increased thickness improves conductivity. That is, as fabric thickness increases, yarn contact area (52) increases and contact resistance decreases. In the example in FIG. 5B, an increase in the contact area (52) between individual yarns is due to an increase in the percentage, or proportion, of miss (M) stitches 34 and tuck (T) stitches 36 with respect to the percentage, or proportion, of single jersey (SJ) stitches 10, and is demonstrated by increased textile thickness. For example, a combination of the SJ/M/T stitches with the miss stitch (34) 15% or less results in a thicker fabric than the SJ/M/T stitch combination with the tuck stitch (36) 15% or less. In some embodiments, fabric thickness can range from about 0.5±0.001 mm and higher. A higher yarn count creates a larger fabric thickness and therefore larger yarn contact areas (52), and thus lower contact resistance and improved conductivity.

Fabric weight (gm/m$^2$): As fabric thickness increases with respect to control of contact resistance so does the fabric weight. Therefore, as fabric thickness increases, fabric weight increases correspondingly, along with the same increase in yarn contact area (52) and decrease in contact resistance. An increase of miss and tuck stitches results in an increase in fabric weight due to the construction of miss stitches 34 and tuck stitches 36 in the knitting process. Miss stitches 34 and tuck stitches 36 cause an excess of yarn (in differing proportions) to build up in the textile structure compared to a single jersey 10 fabric. In some embodiments, fabric weight can range from 100±0.0001 gm.m$^2$ and higher. Embodiments having a larger yarn count (Tex/denier) and thus a larger fabric thickness also have a larger fabric weight, which, in turn, can decrease contact resistance and improve conductivity.

Optical porosity (OP) (% black pixels) is defined as a measure of the light that is transmitted through a fabric when tested using digitized images and analyzed using The University of Texas Health Science Center at San Antonio ImageTool software. Optical porosity provides a quantifiable measure of the cover factor of a fabric. "Fabric cover factor" is defined as the ratio of the area covered by the yarns to the whole area of the fabric. Optical porosity is measured as a ratio of black pixels to white pixels. A decrease in optical porosity corresponds to a decrease in contact resistance. Both miss and tuck stitches are formed when one or more stitches are removed from a plain jersey stitch 10 structure in either the weft (miss stitch 34) direction or warp (tuck stitch 36) direction. As with fabric weight, a change in the percentage, or relative proportion, of SJ/M/T stitches alters the amount of light that is able to pass through the fabric. A plain jersey stitch 10 provides a control structure with a fixed percentage of optical porosity. Thus, a change in the percentage of miss stitches 34 and/or tuck stitches 36 with respect to single jersey stitches 10 causes a change in the contact area (52) between yarns. An increase in tuck stitches 36 or a decrease in miss stitches 34 results in a decrease in optical porosity, depending on the relative percentage of miss stitches 34 and tuck stitches 36. Accordingly, an increase in yarn contact area (52) at rest, and a corresponding decrease in optical porosity, results in a decrease in contact resistance. Therefore, a decrease in optical porosity is directly proportional to a decrease in contact resistance with respect to stitch patterns containing a combination of single jersey stitches 10, miss stitches 34, and tuck stitches 36. Optical porosity can range from 1% black pixels and higher.

Percentage Permanent Stretch (PPS) is defined as a measure of the stretch and recovery of a fabric when subjected to a cyclical load. PPS increases or decreases depending on the percentage of miss stitches 34 and tuck stitches 36 within a particular stitch pattern. PPS relates to both the weft (course) direction 80 and warp (wale) direction 74, and differs for each. The lower the PPS, the higher the optical porosity and therefore the lower the MER/contact resistance. PPS is directly proportional to the percentage of either SJ/M/T stitches present in the textile. Fewer miss stitches 34 in the courses reduce PPS in the weft/course direction 80. Fewer tuck stitches 36 in the wales reduce PPS in the warp/wale direction 74. Percentage Permanent Stretch can range from 25%-2%.

Experiments

The following experiments were conducted to test control of electrical conductivity in various such textile-sensor samples.

Experiments A, B, and C were conducted using the four textile samples in Table 1. Each sample comprises a different stitch pattern (SP). The yarn in each stitch pattern comprises 150 denier, 48 filament, 100% textured, multifilament, polyester coated in a polypyrrole (PPy) intrinsically conducting polymer. Each stitch pattern comprises 50% single jersey (SJ) stitches 10 and a different combination of miss (M) stitches 34 and tuck (T) stitches 36. The percentage of miss stitches 34 and tuck stitches 36 are indicated for each stitch pattern in Table 1. In each of the experiments, a 100% single jersey stitch pattern 10 is used as a control for comparing the four sample stitch patterns (SP-A, SP-B, SP-C, and SP-D).

TABLE 1

| Textile Sample | Percentage of Stitches | | |
|---|---|---|---|
| Stitch Pattern (SP) | Single Jersey (SJ) | Miss (M) | Tuck (T) |
| SP-A | 50% | 5% | 45% |
| SP-B | 50% | 10% | 40% |
| SP-C | 50% | 45% | 5% |
| SP-D | 50% | 40% | 10% |

Experiment A

In Experiment A, mean electrical resistivity (MER), fabric thickness, and optical porosity in the four different sample stitch patterns were compared to those variables in a single jersey 10 fabric. The results of Experiment A, discussed with reference to FIGS. 2, 5A, 5B, 5C, and 6, demonstrate how stitch patterns can be selected to affect these variables so as to optimize contact resistance in a textile.

The table in FIG. 2 shows mean electrical resistivity (MER) values in a single jersey (SJ) stitch pattern 10 control and in the four different sample stitch patterns. MER is shown for each stitch pattern having either relaxed or tensioned courses or relaxed or tensioned wales. Each of the four sample stitch patterns had significantly decreased MER in both the course (horizontal) direction 80 and wale (vertical) direction 74 in comparison to single jersey 10, both in relaxed states and in tensioned states. The discovery that each of the four sample stitch patterns had a significant effect on resting MER in both directions relative to single jersey allows selection of different stitch structures for different sensor types and/or sensing applications. In addition, each sample stitch pattern exhibited a decrease in MER between a relaxed state and a tensioned state, consistent with the effect of increasing yarn contact area (52) related to influence by tuck stitches 36 (such as the tuck loop contact point 46 and the tensioned tuck stitch contact point 50) as the sample was tensioned.

In an embodiment of a method of the present invention, utilizing the resting MER and/or the dynamic range, or change, in MER from a relaxed state to a tensioned state for different stitch percentages allows control of sensitivity in a textile-sensor useful for a particular application. For example, the greater dynamic ranges (76%) in SP-B (10% miss/40% tuck) and (80%) in SP-D (40% miss/10% tuck) allow compressive force measurements over a greater force range. Such stitch patterns can be utilized to optimize contact resistance in a textile-sensor suitable, for example, for measuring compressive force in a sock. The smaller dynamic range (59%) in SP-A (5% miss/45% tuck) allows a more sensitive compressive force measurement for small force ranges. Thus, such a stitch pattern can be utilized to optimize contact resistance in a textile-sensor suitable, for example, for measuring force applied by a compressive bandage to a leg (for example, in the range about 10 mm Hg-60 mm Hg). In addition, the large percentage of miss, or float, stitches 34 (45%) in SP-C is associated with "waisting" in the textile-sensor. Waisting can be defined as the shape (for example, in extreme waisting, an hourglass shape) of a textile due to a higher percentage of miss stitches, which causes a decrease in course length as a result of less interlocking loops within each course. In a textile-sensor having a higher percentage of miss stitches, yarn contact area (52) increases and contact resistance decreases in a quantifiable manner.

Figure 5A:
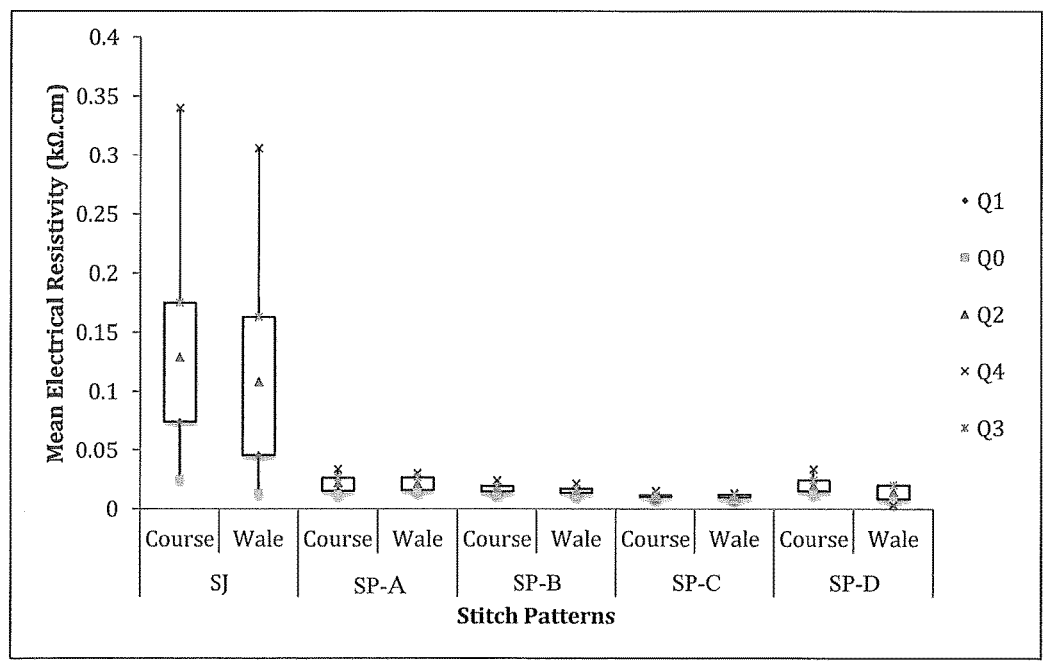
FIG. 5A is a box plot showing variations in MER in the single jersey stitch pattern control and in the four stitch patterns having different percentages of miss and tuck stitches in FIG. 2. The range of MER is shown for each stitch pattern in a relaxed state in both the course direction and the wale direction.

FIG. 5A shows variations in MER in the single jersey stitch pattern 10 control and in the four sample stitch patterns. A number of measurements of MER were taken for each stitch pattern in a relaxed state in both the course direction 80 and the wale direction 74. The measurements were graphed in a box plot to show the ranges of variation. In FIG. 5A, Q0 represents the minimum measurement, Q1 represents the bottom quartile of measurements, Q2 represents the mean measurement, Q3 represents the median measurement, and Q4 represents the maximum measurement.

The range of MER variation in the single jersey stitch pattern 10 control and in the four sample stitch patterns varied depending on the stitch pattern. In particular, the range, or degree, of variation in MER in the single jersey 10 control was much greater than in the four sample stitch patterns. Accordingly, base calibration of resistivity in a single jersey stitch pattern 10 would be more difficult, resulting in a much less reliable textile-sensor structure than a textile-sensor structure having either of the four sample stitch patterns.

Optimizing contact resistance in an electrically conductive yarn or textile can comprise selecting a narrow range of MER variation. As shown in FIG. 5A, SP-B (10% miss/40% tuck) and SP-C (45% miss/5% tuck) exhibited the most narrow ranges of MER variation. Thus, SP-B and SP-C comprise optimized contact resistance suitable for textile-sensor applications requiring greater measurement sensitivity. For example, SP-B and SP-C comprise contact resistance optimized for textile-sensor measurements of light weight pressures.

Fabric thickness is a measure of stitch density. FIG. 5B is a graph showing variations in fabric thickness relative to mean electrical resistivity in courses and in wales for the single jersey stitch pattern control and the four sample stitch patterns. As shown in FIG. 5B, as fabric thickness increases, MER decreases. In particular, the various combinations of miss stitches 34 and tuck stitches 36 in the four sample stitch patterns cause those stitch patterns to have a greater thickness than the single jersey stitch pattern 10. Accordingly, with the increased fabric thickness, the MER in each of the four sample stitch patterns is lower than in the single jersey stitch pattern 10 control, as measured in the course direction 80 and in the wale direction 74.

Figure 5C:
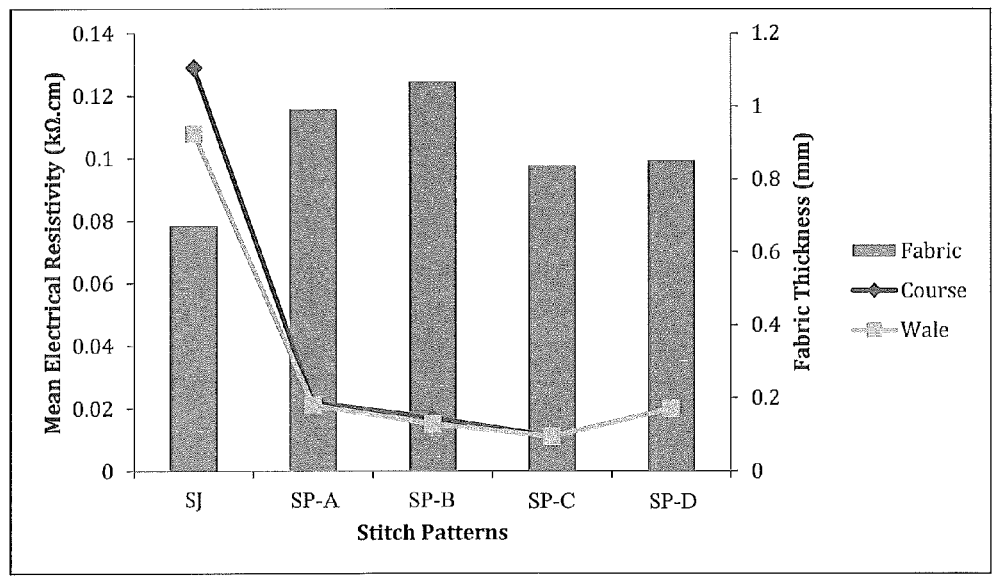
FIG. 5C is a graph showing variations in optical porosity relative to mean electrical resistivity in courses and in wales for the single jersey stitch pattern control and the four stitch patterns having different percentages of miss and tuck stitches in FIG. 2.
Figure 5C:
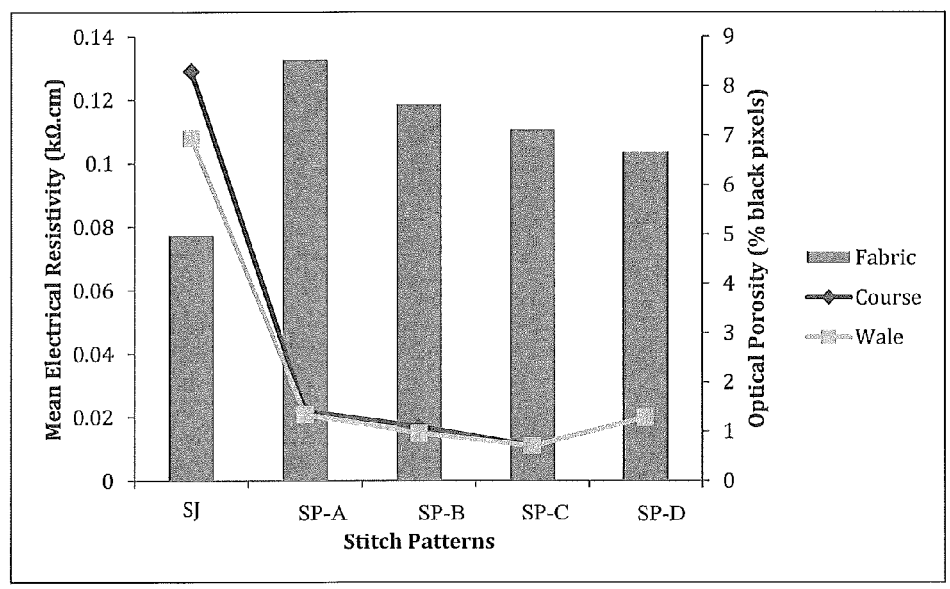

Likewise, optical porosity is a measure of stitch density. FIG. 5C is a graph showing variations in optical porosity relative to mean electrical resistivity in courses and in wales for the single jersey stitch pattern 10 control and the four sample stitch patterns. As optical porosity decreases (less light penetration), MER decreases, as shown in FIG. 5C. In particular, the various combinations of miss stitches 34 and tuck stitches 36 in the four sample stitch patterns cause those stitch patterns to have a lower optical porosity than the single jersey stitch pattern 10. Accordingly, with the decreased optical porosity, the MER in each of the four sample stitch patterns is lower than in the single jersey stitch pattern 10 control, as measured in the course direction 80 and in the wale direction 74.

Figure 6:
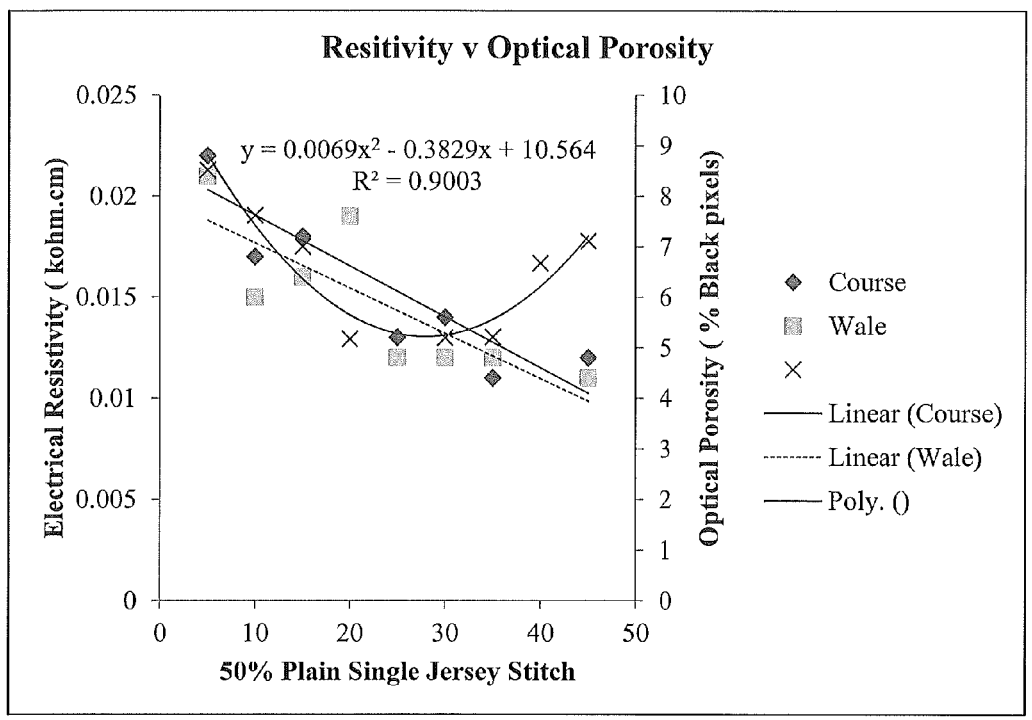
FIG. 6 is a graph showing variations in optical porosity relative to mean electrical resistivity in courses and in wales for a 50% plain single jersey stitch pattern.

FIG. 6 is a graph showing variations in optical porosity relative to mean electrical resistivity in courses and in wales for a 50% plain single jersey stitch pattern 10. As shown in FIG. 6, when increasing amounts of tuck stitches 36 and miss stitches 34 are added to a 50% single jersey stitch pattern 10, optical porosity decreases and electrical resistivity decreases.

Thus, fabric thickness and optical porosity, as measures of stitch density, were tested for correlations with MER. As shown in FIGS. 5B, 5C, and 6, it was discovered that both fabric thickness and optical porosity are strongly correlated with MER in a reliable manner across stitch patterns having different combinations of miss stitches 34 and tuck stitches 36. As a result, both fabric thickness and optical porosity can be utilized as simple measures in optimization of contact resistance in electrically conductive yarns and textiles. For example, a lower optical porosity in a fabric is associated with a greater contact area (52) between yarns (and lower MER) and therefore greater control of contact resistance. In other words, a more closed (more dense) stitch pattern having a lower optical porosity and greater yarn contact area (52) has greater measurement sensitivity in a textile-sensor than a more open (less dense) stitch pattern having a higher optical porosity and less yarn contact area (52). Thus, a more closed (more dense) stitch pattern having a lower optical porosity comprises optimized contact resistance suitable for textile-sensor applications requiring greater measurement sensitivity, such as for measurements of light compressive pressures or small tensile forces.

Experiment B

In Experiment B, four fabric swatches, approximately 100 mm×100 mm in size, were knitted on a Shima Seiki WHOLEGARMENT™ 14gg knitting machine. "GG" represents "gauge" of a knitting machine, and corresponds to the number of needles/inch. The yarn in each sample swatch was a spun staple fiber yarn (80% PES/20% INOX®), commercially available as "S-Shield" from Schoeller. Each swatch was knitted using a different percentage combination of plain jersey stitches 10, tuck stitches 36, and miss stitches 34 (stitch patterns SP-A, SP-B, SP-C, and SP-D).

Figure 7:
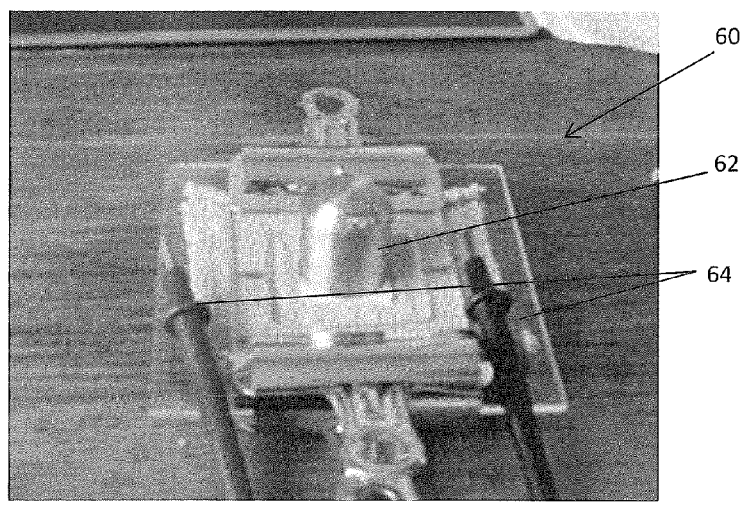
FIG. 7 is perspective view of a test rig used to measure the effects of weight, or pressure, on stitch patterns having different percentages of miss and tuck stitches in the wale (vertical) direction and in the course (horizontal) direction.

Individual sample swatches were then placed under weights in a test-rig 60, as shown in FIG. 7. The test rig 60 was constructed using 3 mm thick polymethyl methacrylate. Two stainless steel weights 62 were used, one weighing 150 gm, the other weighing 250 gm. The weights 62 were separated from the sample swatches by a non-conducting cardboard layer. One weight 62 remained in placed on the sample being tested as a base weight to keep the area under pressure identical for each measurement. Each individual sample swatch was tested for electrical resistance measured with a Q-1559 multimeter (available from Dick Smith Electronics) using two standard multimeter probes 64. So as to compare data from both experiments, measures of electrical conductivity in Experiments B and C were taken as measurements of resistance, rather than resitivity, due to difficulty in obtaining accurate measurement of length under a person's foot in Experiment C. Baseline resistance measurements were taken for each sample swatch without any weight 62 being applied. Ten resistance measurements were taken for each sample in a random manner under 150 gm of weight and under 400 gm of weight. The 400 gm of weight was applied by using the 150 gm weight 62 and the 250 gm weight 62 together. Measurements were taken with the multimeter probes 64 separated 28 mm and with an approximate pressure of 600 Pascal units (Pa) for the 150 gm of weight and an approximate pressure of 1000 Pa for the 400 gm of weight.

Figure 8:
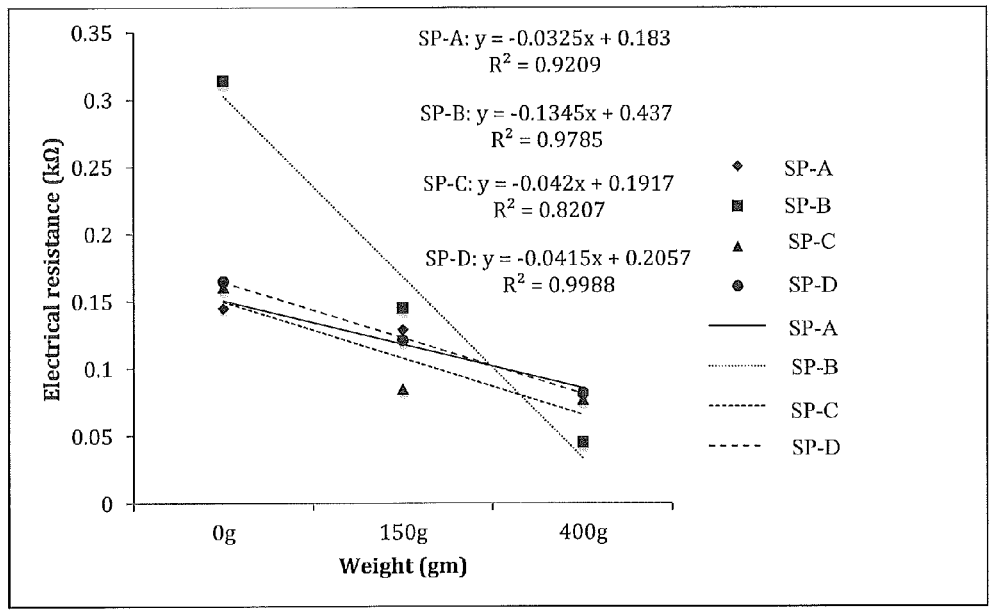
FIG. 8 is a graph showing variations in electrical resistance caused by different amounts of weight in the course (horizontal) direction for swatches of the four stitch patterns having different percentages of miss and tuck stitches in FIG. 2.
Figure 9:
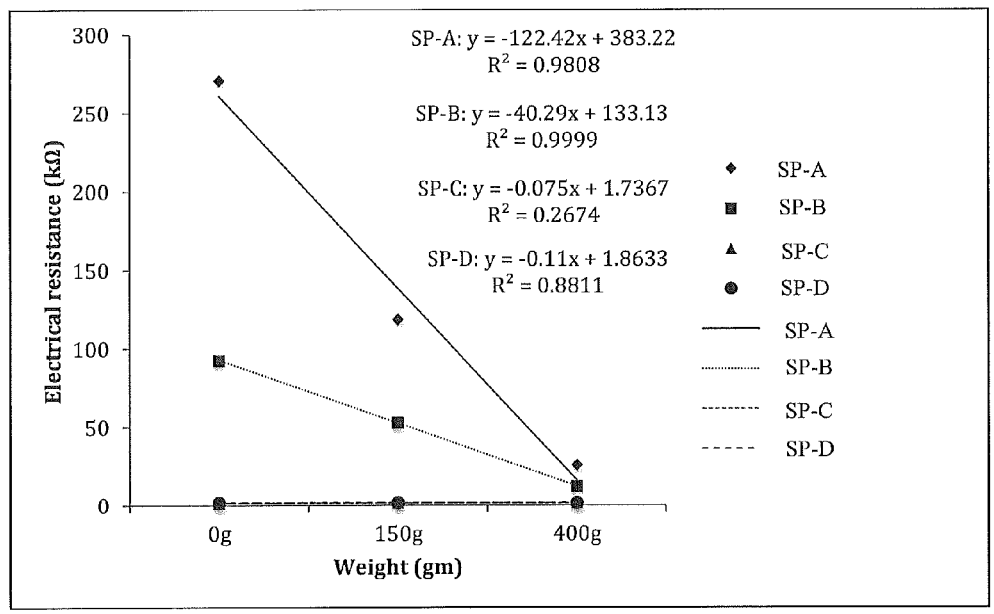
FIG. 9 is a graph showing variations in electrical resistance caused by different amounts of weight in the wale (vertical) direction for swatches of the four stitch patterns having different percentages of miss and tuck stitches in FIG. 2.

The results from Experiments B are represented graphically in FIGS. 8 and 9. FIG. 8 shows electrical resistance for baseline and for the 150 gm of weight and the 400 gm of weight in the course (horizontal) direction 80 for each sample swatch. FIG. 9 shows electrical resistance for baseline and for the 150 gm of weight and the 400 gm of weight in the wale (vertical) direction 74 for each sample swatch.

For the results shown in both FIGS. 8 and 9, the coefficient of determination, denoted $R^2$, was calculated. $R^2$ indicates how well data points fit a statistical model, that is, a measure of how well observed outcomes are replicated by the model. In this instance, a high $R^2$ value, or data fit, indicates a good linear relationship between the variables. With respect to these experiments, a high $R^2$ value for a particular sample stitch pattern means that a textile-sensor comprising that stitch pattern can be utilized to measure weight/pressure in a reliable/repeatable manner.

The $R^2$ values for stitch samples SP-A and SP-B are high for both the horizontal (course) direction 80 shown in FIG. 8 and the vertical (wale) direction 74, as shown in FIG. 9. Both SP-A (5% miss/45% tuck) and SP-B (10% miss/40% tuck) include a large proportion of tuck stitches 36, which serve to increase yarn contact area (52), and thus decrease—and thereby control—contact resistance, in both the vertical direction 74 and horizontal direction 80. Accordingly, stitch samples SP-A and SP-B demonstrate the best fit among samples tested for optimizing contact resistance in textile-sensors in accordance with the present invention.

In particular, the steeper gradient in the linear response by SP-B shown in FIG. 8 demonstrates a greater dynamic range in the course (horizontal) direction 80. Therefore, SP-B has a greater sensitivity to smaller amounts of weight in the course (horizontal) direction. Likewise, the steeper gradient in the linear response by SP-A shown in FIG. 9 demonstrates a greater dynamic range in the wale (vertical) direction 74. Therefore, SP-A has a greater sensitivity to smaller amounts of weight in the wale (vertical) direction 74.

Experiment C

In Experiment C, two fabric swatches, approximately 300 mm×100 mm in size, were knitted on a Shima Seiki WHOLEGARMENT™ 14gg knitting machine. The yarn in each sample swatch was a spun staple fiber yarn (80% PES/20% INOX®), commercially available as "S-Shield" from Schoeller. Each swatch was knitted using a different percentage combination of plain jersey stitches 10, tuck stitches 36, and miss stitches 34 (stitch patterns SP-A and SP-B).

This experiment involved two human subjects. Subject 1 was female weighing 61 kg and subject 2 was male weighing 79 kg. Each subject stood, balanced only on her/his right foot, on the fabric swatches comprising the sample stitch patterns. Each subject wore a sock made from a non-conducting fiber. Each fabric swatch was tested for electrical resistance at two locations—at a line directly below the ankle and at a point approximating the ball of the foot).

Resistance was measured on a Q-1559 multimeter (available from Dick Smith Electronics) using two standard multimeter probes 64. Ten resistance measurements were taken for each sample in a random manner at the two locations for each subject. A probe measuring separation of 70 mm was used for the ankle measurement, and a 100 mm separation was used for the ball of the foot measurement.

Figure 10:
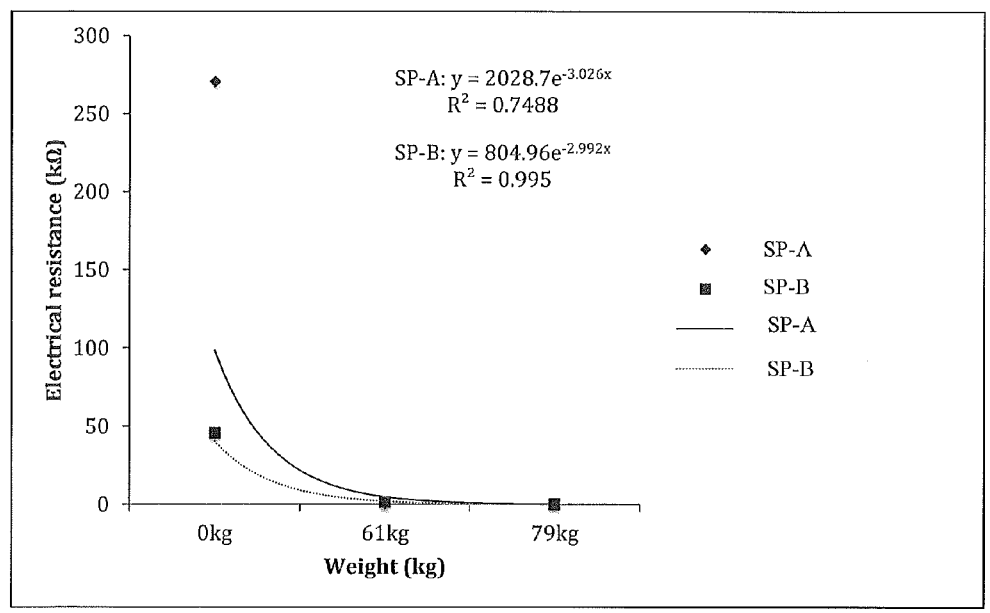
FIG. 10 is graph showing electrical resistance at a line directly below the ankle in the wale (vertical) direction for each of two sample stitch patterns having different percentages of miss and tuck stitches.
Figure 11:
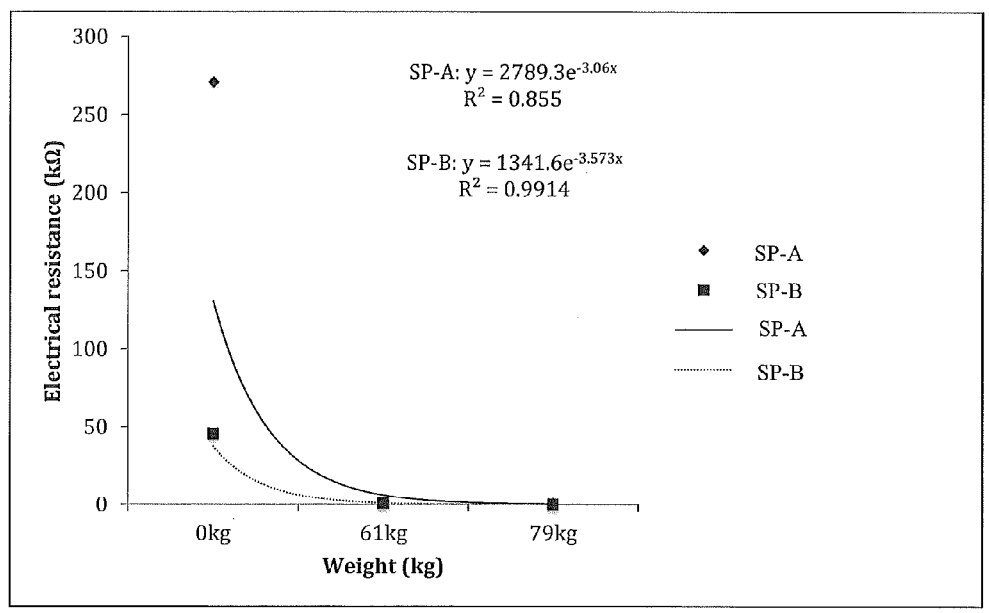
FIG. 11 is a graph showing electrical resistance at a line along the ball of the foot in the wale (vertical) direction for each of two sample stitch patterns having different percentages of miss and tuck stitches.

The results from Experiments C are represented graphically in FIGS. 10 and 11. FIG. 10 shows electrical resistance at a line directly below the ankle in the wale (vertical) direction 74 for each sample swatch. FIG. 11 shows electrical resistance at a line along the ball of the foot in the wale (vertical) direction 80 for each sample swatch.

A logarithmic regression, rather than linear regression, was used for the human-based results in Experiment C due to the large difference in mass applied to the sample fabric swatches as compared to that applied to the sample fabric swatches in Experiment B. Based on the $R^2$ values for resistance measured at both the ankle shown in FIG. 10 and at the ball of the foot shown in FIG. 11, stitch sample SP-B demonstrates the best fit for use in certain embodiments of the textile-sensor in accordance with the present invention. In particular, the more shallow gradient in the logarithmic response by SP-B shown in FIGS. 10 and 11 demonstrates a greater response to larger amounts of weight. Therefore, stitch pattern SP-B provides a suitable textile-sensor for measuring pressure exerted by the human form. Considering the results of both Experiments B and C, it was found that stitch patterns SP-A and SP-B each provide optimized control of contact resistance useful in textile-sensors for measuring weight in different sized objects.

The findings of Experiments A, B, and C together demonstrate that making selections related to variables such as stitch pattern, stitch percentages, electrical resistivity, optical porosity, and fabric thickness can optimize contact resistance in electrically conductive yarns and textiles. Such a method can thus be utilized to reliably predict and control electrical conductivity capabilities in a textile structure and to design textile-sensors useful in a variety of applications. For example, a stitch pattern such as SP-B (10% miss/40% tuck) having: (1) a relatively large dynamic range in MER from a relaxed state to a tensioned state allows compressive force measurements over a greater force range; (2) a narrow range of MER variation allows textile-sensor applications requiring greater measurement sensitivity; and (3) a relatively large dynamic range in MER in the course direction allows measurements in which a greater sensitivity to smaller amounts of weight in the horizontal direction are desired. Thus, a method of selecting stitch pattern, stitch percentage, and other physical stitch, yarn, and/or textile variables provides control of electrical conductivity in textiles such that predictable ranges and/or sensitivities of sensors can be constructed for particular uses.

Experiment D

Figure 13:
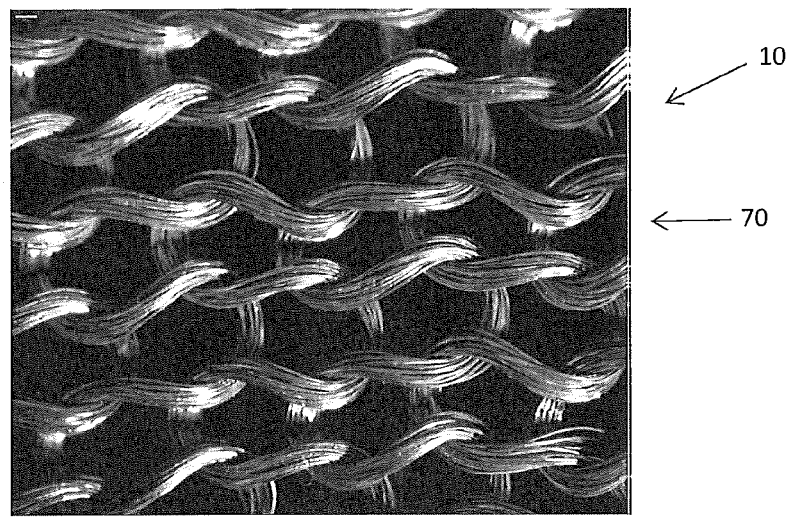
FIG. 13 is an electron microscope photograph of a fabric sample comprising a multi-filament, twisted polyester yarn coated with silver knit in a plain single jersey stitch pattern in an un-deformed state.
Figure 14:
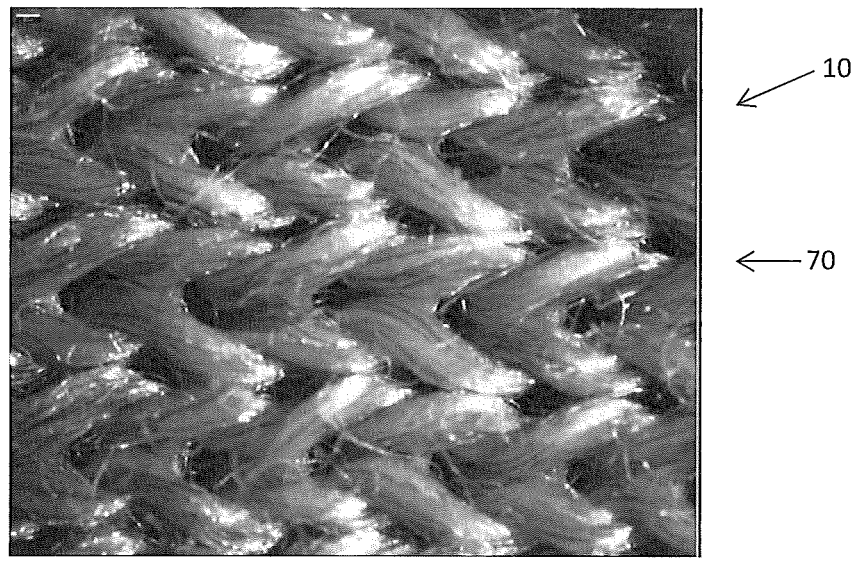
FIG. 14 is an electron microscope photograph of a fabric sample comprising a stainless steel staple fiber spun yarn knit in a plain single jersey stitch pattern in an un-deformed state.

Experiment D was conducted to determine the effects fabric deformation on the shape of yarn contact areas (52). In Experiment D, two fabric samples were tested. Sample A comprises a multi-filament, twisted polyester yarn coated with silver knit in a plain, single jersey stitch pattern. FIG. 13 is an electron microscope photograph of Sample A in an un-deformed state. Sample B comprises a spun staple fiber yarn (80% PES/20% INOX®) in a plain, single jersey stitch pattern 10. FIG. 14 is an electron microscope photograph of Sample B in an un-deformed state. In testing, measurements of multiple yarn units were taken, and descriptions of geometric parameters refer to average measurements in a sample.

Figure 12:
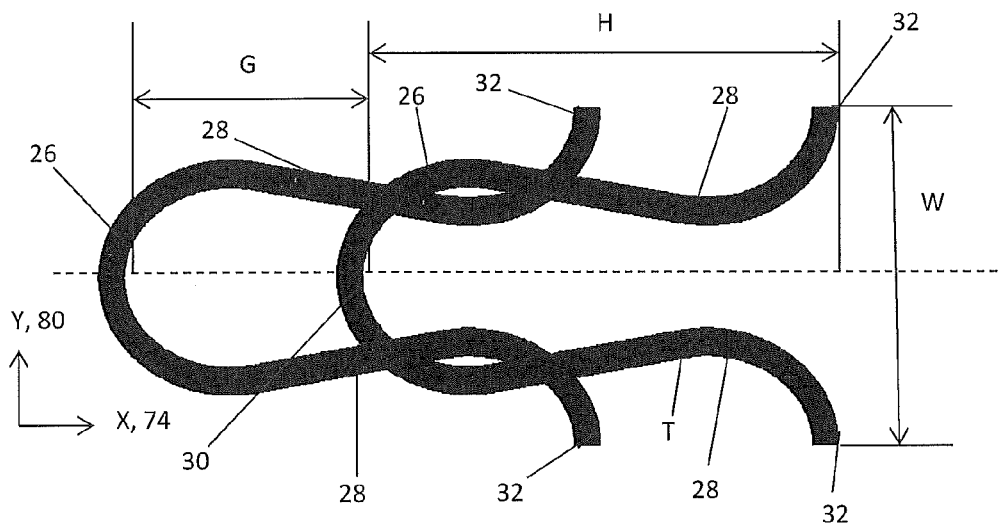
FIG. 12 is a diagrammatic view of the two interconnected yarn units in a single jersey knit stitch pattern shown in FIG. 1, showing yarn unit width, height, gap, and thickness.

The two fabric samples were first compared in an un-deformed state with respect to four geometric parameters of a yarn unit—width, height, gap, and thickness, as shown in FIG. 12. In a single jersey knit 10 fabric, the needle loop 22, or yarn unit, comprises the head 26 and two side legs 28 that form the noose 30. At the base of each leg 28 is a foot 32, which meshes through the head 26 of the loop 24 formed at the previous knitting cycle. The leg 28 of the needle loop 22 passes from one side (or face) to the other side/face of the sinker loop 24 across the leg 28 and head 26 of the sinker loop 24, and then loops around to pass back across the head 26 and opposite leg 28 of the sinker loop 24 to back to the original side/face of the sinker loop 24.

Yarn unit width (W) is defined as the distance between two feet 32 of a single loop 22 or 24. Yarn unit height (H) is defined as the distance between the head 26 and the foot 32 of a single loop 22 or 24. Yarn unit gap (G) is defined as the distance between the head 26 of one loop 22 and the head 26 of the adjacent loop 24 in the same wale. Yarn thickness (T) is defined as the diameter of a yarn. Sample A has a more open knit structure, that is, a larger yarn unit width (W) and height (H) than Sample B. The yarn unit gap (G) is similar in the two samples. Sample B is thicker than Sample A.

The two samples were then compared in deformed states by stretching the samples first in the wale direction 74 (along the x-axis) and then in the course direction 80 (along the y-axis). "Stretching strain," or the degree of stretching, is defined as the ratio of yarn unit (loop) 22, 24 elongation to initial height. Sample A was tested under a similar strain as Sample B, as well as under a higher strain. The two samples were compared in each state of deformation with respect to the four geometric parameters.

When the samples were stretched in the wale direction 74 (along the x-axis), the heads 26 of yarn loops 22 or 24 in one course were pulled tighter about the legs 28 and feet 32 of loops 22 or 24 in the adjacent course. As a result, the yarn unit width (W) decreased significantly. During walewise stretching, yarn unit height (H) did not change significantly, but yarn unit gap (G) increases substantially. Yarn thickness (T) remained relatively unchanged.

Figure 15:
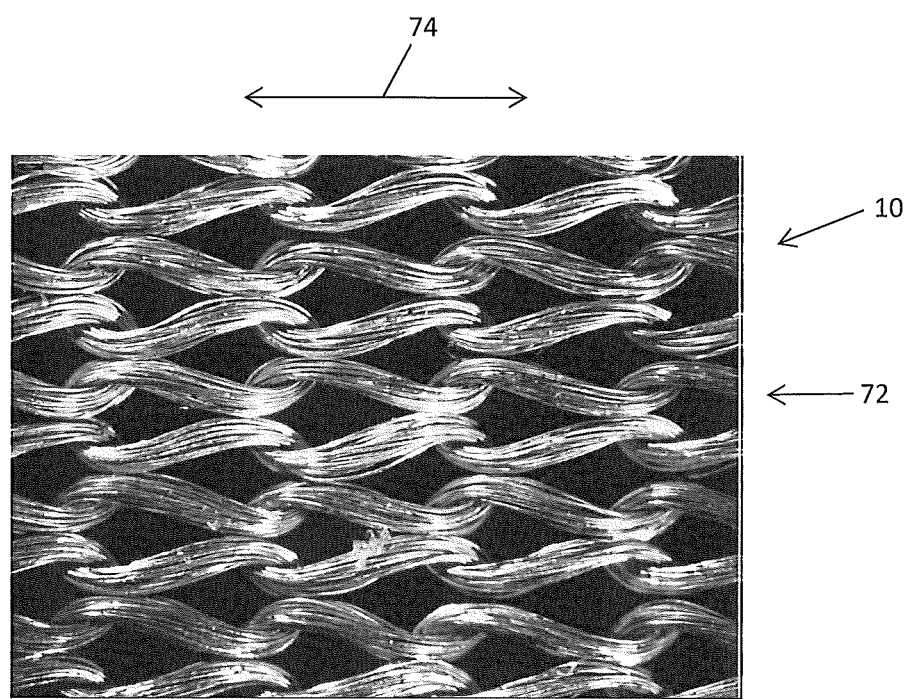
FIG. 15 is an electron microscope photograph of the fabric sample in FIG. 15 under a 22% strain in the wale direction, showing enhanced yarn contact compared to the un-deformed state.

For Sample A, under a walewise strain of 11%, yarn unit width (W) decreased about 19%, and the yarn unit gap (G) increased by about 16%, from comparative dimensions in the un-deformed state. Under an 11% strain, the yarns contact at a few points. Under a walewise strain of 22%, yarn unit width (W) decreased about 39%, and the yarn unit gap (G) increased by about 26%, from the comparative dimensions in the un-deformed state. The photograph in FIG. 15 shows Sample A under a 22% strain 72 in the wale direction 74. Under the 22% strain 72, the yarns contact at every stitch. Thus, under loading in the wale direction 74, a decreasing yarn unit width (W) and an increasing yarn unit gap (G) correlate with increasing yarn contact.

Therefore, under load in the wale (vertical) direction 74, a decrease in yarn unit width (W) results in a less optically porous textile. As light penetration decreases and optical porosity increases, MER decreases. Accordingly, optical porosity can be used as an index of sensitivity to compressive or tensile force under load in the wale (vertical) direction 74 in an embodiment of a method for controlling contact resistance in a textile-sensor. Applying these results, a more closed (more dense) stitch pattern having a higher optical porosity comprises optimized contact resistance suitable for textile-sensor applications requiring greater measurement sensitivity, such as for measurements of light compressive pressures or small tensile forces. Therefore, a textile-sensor having a small yarn unit width (W) and corresponding higher optical porosity can be knit to increase contact resistance for such an application.

Figure 16:
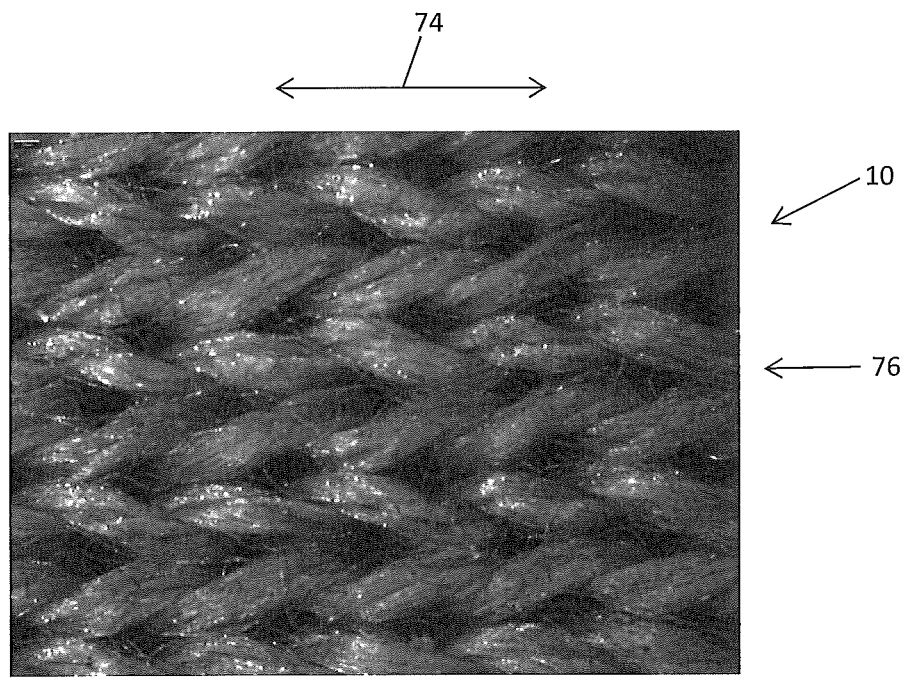
FIG. 16 is an electron microscope photograph of the fabric sample in FIG. 16 under an 11% strain in the wale direction, showing similar yarn contact as in the un-deformed state.

For Sample B, under a walewise strain of 11% (76), yarn unit width (W) decreased by about 1%, yarn unit height (H) increased by about 3%, and yarn unit gap (G) increased by about 3%, from comparative dimensions in the un-deformed state. The photograph in FIG. 16 shows Sample B under an 11% strain 76 in the wale direction 74, showing similar yarn contact as in the un-deformed state. Sample B is significantly more compact than Sample A. That is, Sample B has a greater yarn unit thickness (T), and a smaller yarn unit width (W), yarn unit height (H), and yarn unit gap (G) than Sample A. As a result, Sample B has substantial yarn contact within a stitch even before deformation, or loading. As a result, the variation in geometric parameters for Sample B during loading in the walewise direction 74 is not as significant as for Sample A.

When the samples were stretched in the course direction 80 (along the y-axis), the legs 28 of the yarn loops 22, 24 were pulled apart from one another, such that the yarn unit width (W) increased. In addition, the yarn unit height (H) and the yarn unit gap (G) each decreased. Yarn thickness (T) remained relatively unchanged.

Figure 17:
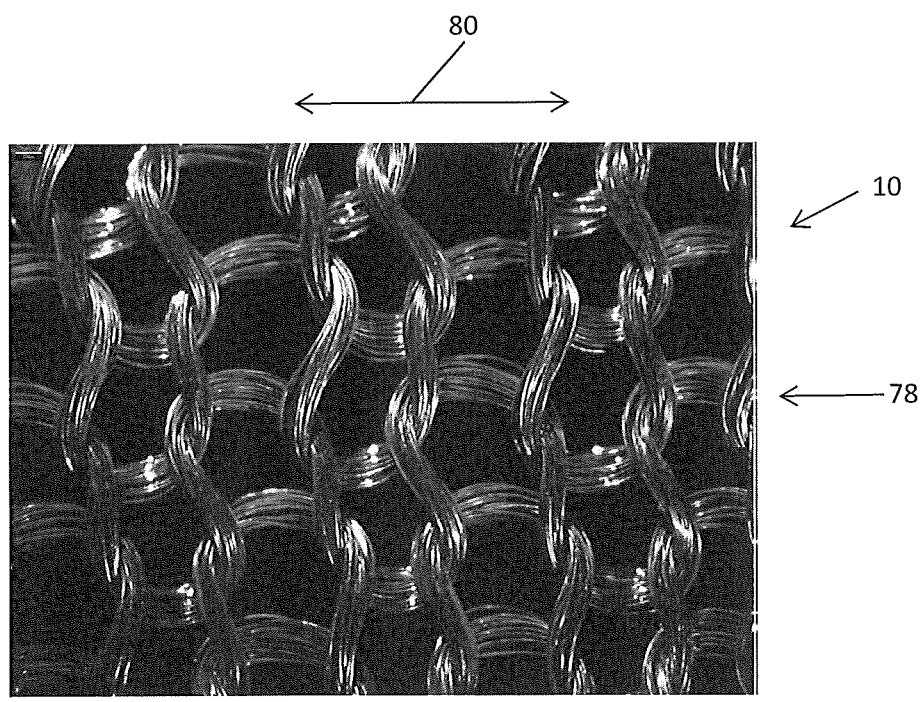
FIG. 17 is an electron microscope photograph of the fabric sample in FIG. 15 under a 20% strain in the course direction, showing decreased yarn contact compared to the un-deformed state.

For Sample A, under a coursewise strain of 13%, yarn unit width (W) increased about 5%, yarn unit height (H) decreased about 14%, and yarn unit gap (G) decreased about 11%, from comparative dimensions in the un-deformed state. Under a coursewise strain of 20% (78), yarn unit width (W) increased about 13%, yarn unit height (H) decreased about 15%, and yarn unit gap (G) decreased about 12%, from comparative dimensions in the un-deformed state. The photograph in FIG. 17 shows Sample A under a 20% strain 78 in the course direction 80. As strain increased in the coursewise direction 80, yarn loops 22, 24 spread apart, causing less yarn contact. Thus, under loading in the coursewise direction 80, an increasing yarn unit width (W), and a decreasing yarn unit height (H) and yarn unit gap (G) correlate with decreasing yarn contact.

Figures 18, 19:
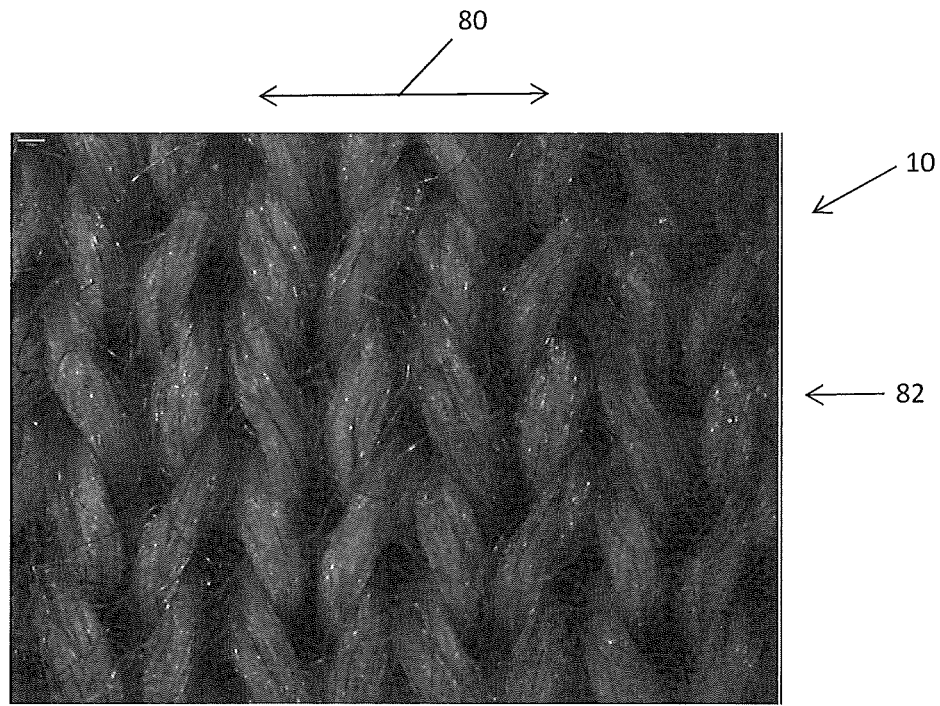
FIG. 18 is an electron microscope photograph of the fabric sample in FIG. 16 under a 12.5% strain in the course direction, showing slightly less yarn contact compared to the un-deformed state.
FIG. 19 is a table showing measured resitivities for each of a polyester and a merino wool sample at each of the seven tested temperatures.

For Sample B, under a coursewise strain of 12.5% (82), yarn unit width (W) increased about 11%, yarn unit height (H) had substantially no change, and yarn unit gap (G) decreased about 3%, from comparative dimensions in the un-deformed state. The photograph in FIG. 18 shows Sample B under a 12.5% strain 82 in the course direction. Sample B has substantial yarn contact within a stitch even before deformation, or loading. As a result, as with loading in the walewise direction 74, the variation in geometric parameters for Sample B during loading in the coursewise direction 80 is not as significant as for Sample A.

That is, under load in the course (horizontal) direction 80, an increase in yarn unit width (W) results in a decrease in optical porosity and a decrease in MER (decreased contact resistance). Accordingly, optical porosity can be used as an index of sensitivity to compressive or tensile force under load in the course (horizontal) direction 80 in an embodiment of a method for controlling contact resistance in a textile-sensor.

Experiment E

Thirty-three (33) sample fabrics each having a different stitch percentage of single jersey stitches 10, miss stitches 34, and tuck stitches 36, were tested to determine variations in resistance relative to pressure in different stitch directions 74, 80. The sample fabrics were then tested to determine variations in resistance relative to temperature in different stitch directions 74, 80.

Compression testing: Each sample stitch pattern was tested for the effects of pressure, or loading, in both the course (horizontal) direction 80 and in the wale (vertical) direction 74.

Under horizontal loading, resistance did not change significantly in most stitch patterns. As described herein, contact resistance varies according to the number, size, and shape of contact points in a particular direction 74, 80 of a textile structure. Thus, when there are fewer contact points in the course (horizontal) direction 80, less change in resistance is expected in the horizontal direction 80. For example, a high number of miss stitches 36 (such as the sample stitch pattern having 50% single jersey 10, 35% miss 34, and 15% tuck 36 stitches) results in fewer contact points in the course direction 80. As a result, embodiments of a method for optimizing contact resistance in an electrically conductive yarn and textile can comprise selecting a yarn type and stitch pattern having fewer contact points in a course to provide a horizontal, low measurement sensitivity textile-sensor. Such a textile-sensor can be useful for measuring large compressive loads, such as across the ball of the foot in a sock designed for use in patients with diabetes.

Under vertical loading, resistance did change in many stitch patterns. In particular, testing showed that contact resistance can decrease with increased loading in the wale (vertical) direction 74. Results of testing demonstrated that control of contact resistance relative to pressure is a function of the percentage of stitch type, which influences the number and quality of yarn contact points. For example, one sample stitch pattern having 50% single jersey 10, 40% tuck 36, and 10% miss 34 stitches, a higher percentage of tuck stitches 36 (and thus yarn contact points) than other samples, showed a strong linear relationship between increasing vertical loading and decreasing resistance. As a result, embodiments of a method for optimizing contact resistance in an electrically conductive yarn and textile can comprise selecting a yarn type and stitch pattern having a higher percentage of tuck stitches 36 (and thus yarn contact points) to provide a vertical, high measurement sensitivity textile-sensor. Such a textile-sensor can be useful for measuring vertically-oriented loads such as grip strength and duration or movement of an elbow in a patient undergoing rehabilitation.

It was discovered that under similar loads, resistance values were an order of magnitude higher in the vertical direction 74 than in the horizontal direction 80. This variation is due in large part to the influence of tuck stitches 36, particularly in the vertical direction 74. As described herein with reference to FIGS. 3A and 3B, tuck stitch contact points 44, tuck loop contact points 46, held loop contact points 48, and tensioned tuck stitch contact points 50 create increased yarn contact area (52), and thus provide control over contact resistance in a textile structure. In some embodiments of a method for controlling contact resistance in accordance with the present invention, placement of tuck stitches 36 can be utilized to optimize contact resistance in an electrically conductive textile-sensor in the vertical direction 74 along a wale. In other embodiments, tuck stitches 36 can be placed in multiple wales in a selected area of the fabric so as to optimize contact resistance in a defined area of the textile-sensor. In still other embodiments, selecting a stitch pattern having a particular high percentage of tuck stitches 36 that exhibits decreasing resistance with increasing load in both directions 74, 80, such as the sample stitch pattern having 50% single jersey 10, 40% tuck 36, and 10% miss 34 stitches, contact resistance can be optimized in a textile-sensor in both directions 74, 80. For example, such a stitch pattern can be knit in a defined area in a textile-sensor fabric to create a bi-directional sensing area for a particular use.

Temperature testing: Each of the 33 sample stitch patterns was tested for the effects of temperature on resistance in both the course (horizontal) direction 80 and in the wale (vertical) direction 74. Findings showed that resistance (and thus electrical conductivity) varies in response to changing temperature for different stitch percentages and in different stitch directions 74, 80.

In particular, findings showed that the relationship between temperature and resistance is linear. The samples having the largest percentage of tuck stitches 36 (which have the largest yarn contact area (52)) showed the best relationship (that is, the best $R^2$ fit) between temperature and resistance. Results of testing demonstrated that control of contact resistance relative to temperature is a function of the percentage of stitch type, which influences the number and quality of yarn contact points (42, 44, 46, 48, 50). For example, one sample stitch pattern having 50% single jersey 10, 40% tuck 36, and 10% miss 34 stitches, a higher percentage of tuck stitches 36 (and thus yarn contact points) than other samples, showed a strong linear relationship between temperature and resistance.

As a result, embodiments of a method for optimizing contact resistance in an electrically conductive yarn and textile can comprise selecting a yarn type and stitch pattern having a larger percentage of tuck stitches 36 to provide a temperature-sensitive textile-sensor. Such a textile-sensor can be utilized for measuring ambient temperature in a heat-sensitive industrial environment, such as in a petrochemical production environment. Another embodiment of such a textile-sensor can be utilized for measuring a worker's skin temperature in an industrial setting, such as in steel mill.

Experiment F

Yarn contact area 52 was estimated for Samples A and B in their undeformed state. Yarn contact area 52 was estimated along the three-dimensional interface between yarns using microscopic photography. Contact length was measured along the interface between the head 26 and legs 28 of one yarn loop 22 and the legs 28 and feet 32 of the intermeshed adjacent loop 24. Different viewing angles were used to measure a minimum contact length (l) and a maximum contact length (L) for each of multiple loop interfaces. To accommodate the height (H) of the yarn above the two-dimensional plane of the image, the two-dimensional measured minimum and maximum contact lengths (l, L) were converted to three-dimensional calculated minimum and maximum contact lengths (l, L). The height (H) of the yarn above the two-dimensional plane of the image was approximated as angle $\alpha$, where $\alpha = \arctan(T/H-G)$. A calculated contact length was taken as the measured contact length divided by $\cos(\alpha)$. For Sample A, the average calculated minimal contact length (l) was 692 μm (micrometers), and the average calculated maximum contact length (L) was 942 μm.

In order to measure contact width between yarn loop interfaces, pieces of the fabric samples were mounted into resin and cuts made perpendicular to the x-direction (in the two-dimensional plane of the image). The average contact width in Sample A was 143.5 μm.

The average contact area was then calculated as: Contact Area (CA)=Contact Length (CL)×Contact Width (CW). Using the average calculated minimum and maximum contact lengths (l, L), the average contact area for yarn units in Sample A was estimated to be between 99,302 μm$^2$ and 135,177 μm$^2$.

The contact area density (contact area per unit fabric area) is defined as: Contact Area Density (CAD)=Contact Area (CA)/(W/2×G). Using the average minimum and maximum contact areas and the average yarn unit width (W) and average yarn unit gap (G) in the undeformed geometry, the contact area density in Sample A was calculated to be between 11% and 15%.

For Sample B, the average calculated minimal contact length (l) was 986 μm, and the average calculated maximum contact length (L) was 1388 μm. The average contact width in Sample B was 185 μm. Using the average calculated minimum and maximum contact lengths (l, L), the average contact area for yarn units in Sample B was estimated to be between 182,410 μm2 and 256,780 μm2. Using the average minimum and maximum contact areas and the average yarn unit width (W) and average yarn unit gap (G) in the undeformed geometry, the contact area density in Sample B was calculated to be between 28% and 40%.

The calculated yarn contact area densities for Samples A and B demonstrate the difference between the types of yarn in the two samples. Sample A comprises filament yarns intrinsically having less yarn contact points (42, 44, 46, 48, 50) and therefore less yarn contact area 52 than staple fiber yarns. Fewer contact points (42, 44, 46, 48, 50) (less yarn density) provide a relatively higher contact resistance and thus less sensitivity to compressive and tensile force. In an embodiment of a method for controlling contact resistance in an electrically conductive textile, selecting a smaller yarn contact area 52 can be useful for measuring large mass/pressure differences, for example, point pressures in a foot-pad sensor.

Sample B comprises staple fiber yarns (typically about 25-35 mm in length) intrinsically having more yarn contact points (42, 44, 46, 48, 50) and therefore more yarn contact area 52 than filament yarns. More contact points (42, 44, 46, 48, 50) (greater density) provide a relatively lower contact resistance and thus greater sensitivity to compressive and tensile force. In an embodiment of a method for controlling contact resistance in an electrically conductive textile, selecting a larger yarn contact area 52 can be useful for measuring small mass/pressure differences, for example, "feel" in the fingertips of gloves used in prosthetic hands and arms.

In some embodiments, contact resistance in electrically conductive yarns can be optimized in weft-knitted textile structures. In a weft-knitted fabric, one continuous yarn runs widthwise across the fabric and forms all of the loops 22, 24 in each course. Weft knit fabrics can be produced on both flat and circular knitting machines. In other embodiments, contact resistance in electrically conductive yarns can be optimized in warp-knitted textile structures. In a warp-knitted fabric, one or more yarns generally run lengthwise in a zigzag pattern, which forms interlacing loops 22, 24 in two or more wales.

An electrically conductive textile having optimized contact resistance in accordance with the present invention can sense, or detect, a variety of variables in a person or object on which the textile is placed. For example, such a textile may sense physiological changes in a person wearing the textile. The detected change in a variable can be transmitted for monitoring, recording, and/or feedback. The sensed data may be in the form of an electrical signal. The signal transmission may be from the textile-sensor to a device on the textile and/or to another location. Such transmission or other operation related to the sensed data may be carried out via an electronic interface with the textile-sensor.

Embodiments of the present invention can include such an electronic interface with the textile-sensor. The electronic interface can include one or more of electronic circuitry configured to receive power from a power source, electronic circuitry configured for data transmission, an electronic device disposed on, mechanically affixed to, or integrated with the textile-sensor, a wired and/or wireless coupling between the textile-sensor and a portable electronic device, and/or other configurations to cooperate with any of a variety of different wearable or remote electronics. Such electronic interface is designed to avoid compromising the comfort and/or durability of a garment comprising the textile-sensor.

In one aspect of the present invention, the textile itself, having contact resistance optimized, acts as a sensor. Some embodiments of such a textile-sensor can measure variables or parameters such as tensile force, compressive force, movement, and temperature. Accordingly, various embodiments of such a textile-sensor can have different specific functionalities and applications. Embodiments of such a textile-sensor can include functionalities and applications related to, for example, (1) medical compression garments, (2) athletic compression garments, (3) hospital bed and/or wheelchairs, (4) commercial furniture, such as office chairs, (5) fit of face masks, (6) cardiac monitoring; (7) EMG monitoring; (8) sensing temperature; (9) prosthetic limb enhancement; (10) sensing movement; (11) sensing force; and (12) intelligent bandages.

Some embodiments of a textile-sensor having optimized contact resistance can have applications in medical compression garments. In one embodiment, the textile-sensor can comprise a compressive pressure garment, such as a sock, that can be placed over a wound dressing. Using a resistive sensor configuration in the textile-sensor to measure compressive force, the compression sock can determine the average pressure applied across the sensor and transmit that information to a display device.

The ability to unobtrusively monitor the compressive pressure applied by such a sock to each patient allows for more consistent application of the desired level of compression to individual patients. Individualized compressive pressure therapy can lead to improved wound recovery, shorter healing time with reduced costs, and reduced risk of damage to the leg from excessive compression. Such an embodiment overcomes a major limitation in conventional compression bandage product design—that is, that the compression level applied by a compression sock varies depending on the limb size of the patient (governed by physical laws such as Laplace's equation). For example, if the same product were used by ten different patients, each would experience a different actual applied compression level due to individual limb size variations.

In some embodiments, the textile-as-sensor can be integrated into compression hosiery to monitor product lifecycle and alert the user when a new compression product is indicated or desired. In addition, the textile-as-sensor can provide for continuous monitoring of compressive force during the period of medical necessity.

Some embodiments of a textile-sensor having optimized contact resistance can have applications in athletic compression garments. In some embodiments, the textile-sensor can be integrated into athletic compression garments to allow customer visualization of the desired correct compression at point-of-purchase. In addition, such a textile-sensor athletic compression garment can allow monitoring of the product lifecycle and alert the user when a new compression product is desired.

Some athletic garment embodiments comprise a vest capable of measuring physiological parameters for training. The vest can be capable of transmitting biological data to a smart phone, watch, or other visual display. Such a vest can monitor physiological metrics, including, for example, respiration rate, respiration volume, heart rate, and/or oxygen saturation.

Some embodiments of a textile-sensor having optimized contact resistance can have applications in hospital beds and/or wheelchairs. In some embodiments, the textile-sensor can be integrated into a hospital bed and/or wheelchair fabric, or into fabric in commercial furniture, such as office chair fabric, in which the fabric surface is able to monitor temperature and/or compression. A layer of fabric with customised sensor size and shape can enable a patient or health care provider to detect when the patient is at risk of developing pressure ulcers from points of excessive pressure.

Some embodiments of a textile-sensor having optimized contact resistance can have applications in fitting of face masks. In some embodiments, the textile-sensor can be integrated into medical devices worn by patients both in a clinical and in an "at home" environment. For example, a textile-sensor medical device can comprise a face mask. The face mask textile-sensor can utilize compressive and tensile force measurements to establish proper fit, ensure comfort, and eliminate application of excessive force by the mask which may cause skin lesions. Such face mask textile-sensors can be worn, for example, by health care workers, by first responders, or by those as part of an industrial safety regime.

Some embodiments of a textile-sensor having optimized contact resistance can have applications in cardiac monitoring. Some embodiments of the present invention can comprise an electrically conductive yarn having contact resistance optimized for monitoring cardiac electrical signals. The cardiac sensing yarn can comprise a set, or plurality of sensors, positionable in various locations on a person for optimal sensing of cardiac signals. The cardiac sensing yarn having optimized contact resistance can comprise a stand-alone cardiac monitoring pad, or it can be integrally knit into desired locations in a textile-sensor. In the textile-sensor embodiment, each of the separate sensors can be connected to the other sensors with "wiring" pathways integrated into the textile structure. The cardiac monitor sensors can be connected to an electrocardiographic (ECG) output. Embodiments of the cardiac monitor textile structure can register electrical signals on the skin of both human and animal subjects, and can measure, record, and transmit cardiac waveform. Such a device can be utilized to monitor heart rate and/or ECG, for example, of athletes during activity, or perform ECG monitoring in clinical applications. Accordingly, embodiments of the cardiac monitor textile structure can provide an ambulatory sensing platform for cardiac signals, including monitoring heart rate and/or ECG in medical and.ior athletic applications.

Some embodiments of a textile-sensor having optimized contact resistance can have applications in electromyographic monitoring. Electromyography (EMG) is a technique used to record the electrical activity of skeletal muscles. This technique can use intra-muscular or skin surface electrodes to gather data. EMG as a technique can be used in medical illness, sports injury rehabilitation, as well as assisting in prosthetic integration and robot/human interfaces. In the medical sector, a primary use of EMG is in post stroke rehabilitation. EMG is used as a diagnostic tool to determine muscle strength. However, it may also be used to retrain and re-strengthen targeted muscles and associated neurons. This relatively new field requires physiological data in order to program game scenarios that allow the users to strengthen and retrain damaged muscles and neural pathways.

Some embodiments of a textile structure/sensor having optimized contact resistance according to the present invention may be utilized for electromyographic (EMG) monitoring. For example, such a textile structure may be worn to provide sensory feedback as part of neuromuscular rehabilitation.

Some embodiments of a textile-sensor having optimized contact resistance can have applications in sensing temperature. Some embodiments of a textile-sensor having optimized contact resistance may provide real-time monitoring of human temperature. The placement of such a textile-sensor within an armpit area of a baselayer garment allows real-time monitoring of body temperature and comparison with acceptable clinical parameters. In addition, placement of the textile structure on the exterior of a garment can provide real-time readings of environmental temperatures, which can be compared with health parameters and/or duty of care/safety requirements.

Experiment G illustrates that electrical resistance is dependent upon temperature. Thus, conductivity changes with temperature. Accordingly, an embodiment of a textile structure utilized for monitoring temperature can take expected temperature ranges into account when contact resistance in the textile structure is optimized.

In Experiment G, two uncoated fabric samples of single jersey stitch polyester and single jersey stitch merino wool were coated with polypyrrole (PPy) by vapour phase polymerization. 50 mm×50 mm samples of each fabric were placed in an aqueous solution of Iron (III) chloride (0.8 mol/L) and 1-5-naphthalenedisulfonic acid (0.1 mol/L) for one hour. The samples were removed and air dried. The dried samples were then suspended in a sealed vessel with pyrrole monomer at the bottom and heated to 60° C. for 3 hours. The samples were then removed, washed by warm water, and left to dry overnight.

Figure 20:
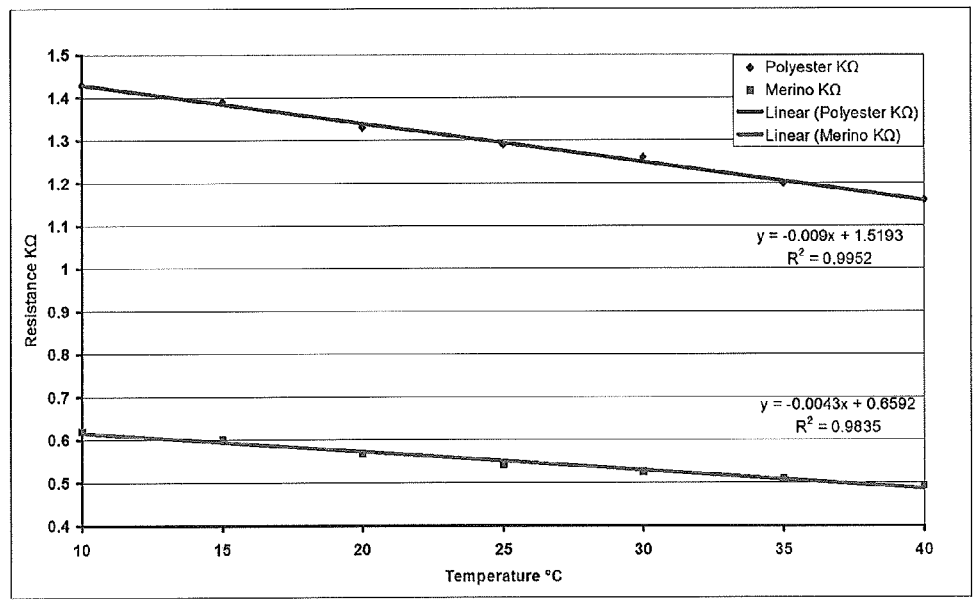
FIG. 20 is a graph showing the resistivity measurements for each fabric sample in FIG. 19 plotted against the temperatures.

Electrical resistivities of the samples were measured at temperatures at five-degree increments between 10° C. and 40° C. under argon by a multimeter connected to two copper strips on the fabric 30 mm apart. These results are shown in FIGS. 19 and 20. FIG. 19 is a table showing the measured resitivities for each of the polyester and the merino wool samples at each of the seven tested temperatures. FIG. 20 is a graph showing the resistivity measurements for each fabric sample plotted against the temperatures. For both fabric samples, there was a linear, inversely proportional relationship between temperature and resistivity. As temperature increased, resitivity decreased. The merino wool sample had resistivity approximately half that of the polyester sample, due to the thicker nature of the wool fabric resulting in a better coating of polypyrrole.

Some embodiments of a textile-sensor having optimized contact resistance can have applications in prosthetic limb enhancement. People with prosthetic limbs lose the ability to "feel" objects. Nerves have been severed and therefore touch is lost. Neural engineering involves clinical implementation of devices in neural prosthesis systems for individuals with diseased or compromised neural systems so that pressures in such a system are transferred to nerve nodes within the surviving part of the limb. An example of such a pressure—nerve node interface is known as "neuromimetic interfaces" between neural tissue and engineered devices. A neuromimetic interface is defined as an electrode, polymer, or other device or material that mimics the mechanical, chemical, and/or electrical properties of neural tissue. An objective of neural engineering is to integrate such devices that behave as though they were natural neural tissue.

Some embodiments of a textile structure having optimized contact resistance according to the present invention can convert such pressures in an affected limb into an electrical signal and transfer those signals to nerve nodes within the surviving part of the limb. In other embodiments, peripheral nerve electrodes can combine electrical and optical stimulation techniques to effect a neuromimetic interface. In still other embodiments, polymeric fiber substrates with mechanical properties similar to neural tissue can be used in, or as, cortical electrodes.

Some embodiments of a textile-sensor having optimized contact resistance can have applications in monitoring movement. Some embodiments of a textile structure having optimized contact resistance according to the present invention can measure movement in a textile by a change in electrical resistance. Sensor placement and shape help determine what movement is measured and how it is measured. In some embodiments, a contact resistance-optimized textile-sensor can provide an average movement, rather than absolute movement. In certain embodiments, the textile-sensor can be combined with another sensor, for example, a conventional capacitance-type sensor. In such a combination, absolute movement can be measured with a high degree of sensitivity.

Examples of types of movement that can be monitored by some embodiments of a contact resistance-optimized textile structure (alone or in combination with another type of sensor) include: (1) simple respiration rate, in medical and/or athletic applications; (2) respiratory tidal volume, in medical and/or athletic applications; (3) limb movement, for example, in medical rehabilitation; (4) limb movement and joint angle, for example, in medical and sports rehabilitation; (5) robotic/human interface, for example, in medical, industrial, and at-risk first responders/military applications; and (6) subsurface monitoring, for example, monitoring structural and/or earthquake-type movement, and monitoring in geotechnical real-time and related to disaster prevention applications.

Some embodiments of a textile-sensor having optimized contact resistance can have applications in monitoring force. Some embodiments of a textile structure having optimized contact resistance according to the present invention can measure both tensile and compressive force by a change in electrical resistance. Such an embodiment can measure absolute compressive force and/or average tensile force. Such an embodiment can be utilized to monitor these forces in applications, including: (1) pressure sensors, in medical and/or athletic applications; (2) compressive medical bandages; (3) limb strength/power, for example, in advanced medical and sports rehabilitation; (4) ambulatory blood pressure monitoring; and (5) subsurface monitoring, for example, in structural and "disaster" forces, geotechnical real-time, and disaster prevention applications.

Some embodiments of a textile-sensor having optimized contact resistance can have applications in intelligent bandages. Some such embodiments of a textile structure can be utilized in production of "intelligent" bandages. Such bandages may sense temperature, force, moisture, and/or pH. In certain embodiments, the contact resistance-optimized textile-sensor can sense microcirculation of limb extremities.

In another aspect of the present invention, embodiments of a method or textile-sensor can comprise a capacitive sensor. "Capacitance" is defined as the ratio of electric charge to potential on an isolated conductor, or the ratio of electric charge on one of a pair of conductors to the potential difference between them. Capacitance is calculated using Gauss' Law. A common form of a capacitor is a parallel plate capacitor. In such a device, capacitance is directly proportional to the surface area of the plates and inversely proportional to the separation distance between the plates. Capacitance can be calculated if the geometry of the conductors and the dielectric properties of the insulator between the conductors are known. For example, the capacitance of a parallel-plate capacitor constructed of two parallel plates both of area A separated by a distance d is approximately equal to the following: $C = \varepsilon r \varepsilon 0 A/d$, where C is capacitance; A is the area of overlap of the two plates; $\varepsilon r$ is the relative static permittivity (sometimes called the dielectric constant) of the material between the plates (for a vacuum, $\varepsilon r=1$); $\varepsilon 0$ is the electric constant ($\varepsilon 0 \approx 8.854 \times 10\text{-}12$ F m-1); and d is the separation between the plates.

In some embodiments, the capacitive textile-sensor 90 can comprise at least two capacitor plate elements 92 in which contact resistance is controlled to provide optimal functioning for a particular sensing activity. Contact resistance can be controlled, and thus optimized, by manipulating variables including physical yarn variables such as yarn type/composition, yarn fabrication method, and yarn count and stitch variables such as stitch type and pattern, stitch length, and stitch percentage. Such variables can affect the number and shape of yarn contact points (42, 44, 46, 48, 50) and thus yarn contact area 52 within the capacitor plate elements 92.

The capacitor plate elements 92 can comprise electrically conductive yarn integrally knit as part of the textile fabric in which they are embedded. Since capacitance is a function of the physical dimensions, or geometry, of the conductors, the functionality of the capacitance sensor 90 relates to the size and geometric shape of electrically conductive yarns that form the capacitor plate elements 92. The capacitor plate elements 92 can be effectively knitted using Shima Seiki technology, which allows a dielectric material to be advantageously knit into the textile during its fabrication. The dielectric material can be placed at any point in the knitting process, and can comprise any shape. Thus, integrally knitting the capacitive sensor 90 as part of the textile fabric during fabrication allows selection of position, size, and shape of the capacitor plate elements 92 and the dielectric material. In this way, the capacitive textile-sensor 90 can be customized for a particular sensor functionality.

When textile fabric comprising the capacitive textile-sensor 90 is stretched, the area covered by two capacitor plate elements 92 changes. When stretch, or strain, is applied along the length of the textile-sensor 90 comprising an integrally knit capacitive sensor, the strain generates capacitance that is linear relative to the strain. Strain on a fabric is directly proportional to a change in length of the fabric. Thus, strain is equal to a change in length divided by the original length. That is, a measure of capacitance correlates with an amount of strain in the capacitive textile-sensor 90. In such embodiments, the electrically conductive yarn preferably comprises a single yarn so that the original length of the yarn can be known with precision.

Figure 21:
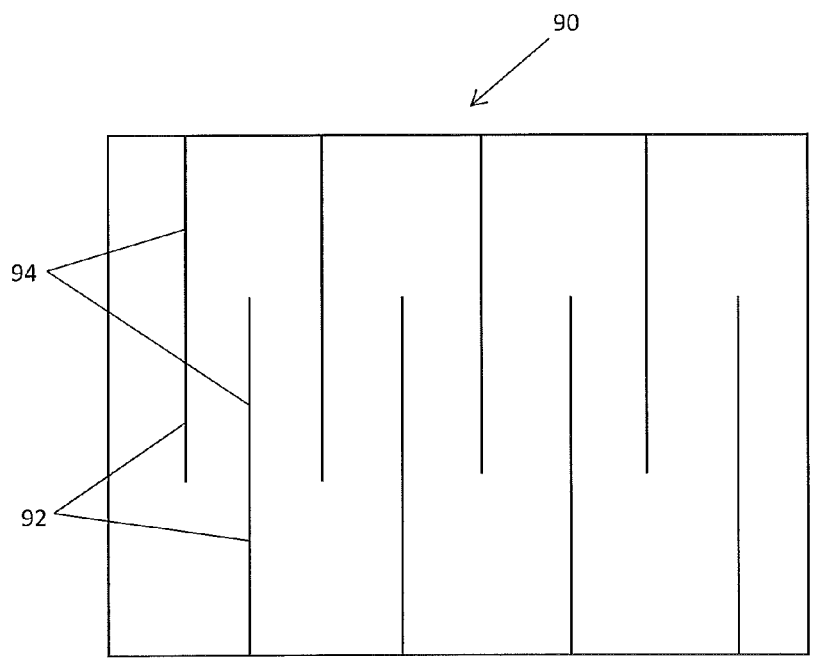
FIG. 21 is a diagrammatic view of a capacitive textile-sensor having a plurality of capacitor plate elements knit as a series of interdigitated fingers, in an embodiment of the present invention.

In one embodiment, the capacitive textile-sensor 90 can be knit as one piece having a plurality of capacitor plate elements 92 comprising electrically conductive yarn knit as a series of interdigitated fingers, as shown in FIG. 21. The electrically conductive yarn can comprise, for example, a silver filament yarn. Capacitance can be measured between adjacent capacitor plate elements/fingers 92.

Figure 22:
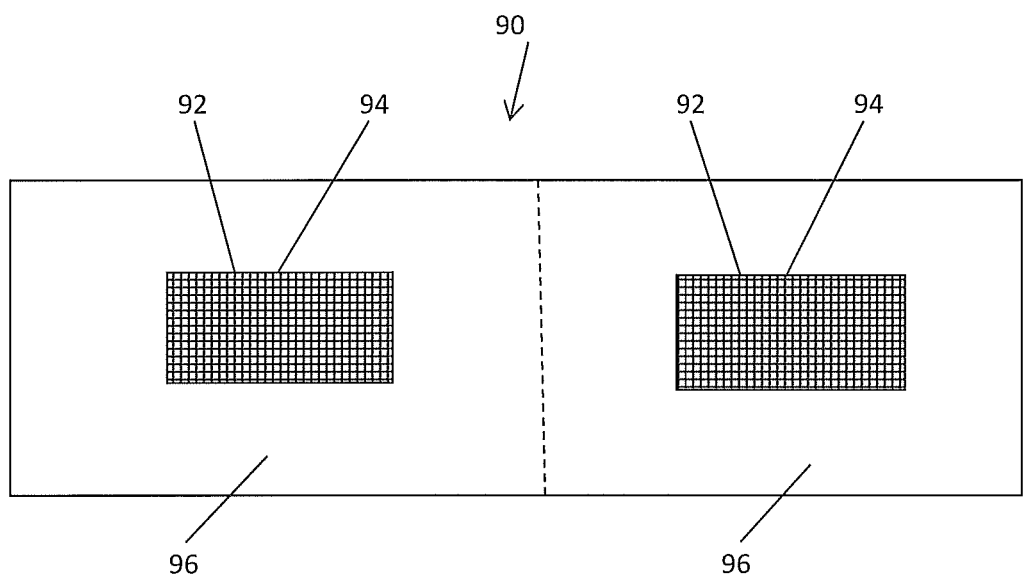
FIG. 22 is a diagrammatic view of a capacitive textile-sensor comprising capacitor plate elements knit into a defined area of two opposable fabric layers, in an embodiment of the present invention.

In another embodiment, the capacitor plate elements 92 can comprise electrically conductive yarn knit into a defined area of two opposable fabric layers, first and second layers 96, 98, respectively, as shown in FIG. 22. In operation, the two fabric layers 96, 98 can simply and easily be placed together, for example, folded onto each other, so that the defined areas of capacitive yarn are spaced in relation to each other sufficient for measurement of capacitance. In the two-layer capacitive textile-sensor configuration, capacitance can be measured in one layer relative to the other layer.

One advantage of such capacitive textile-sensor embodiments is that control of contact resistance in the integrally knit capacitor plate elements 92 allows fine control manipulations of measurement sensitivity. As a result, measurement accuracy is enhanced. For example, the closer the capacitor elements 92, the more accurate the capacitance measurements. In embodiments of the capacitive textile-sensor 90, the capacitor elements 92 are knit so that adjacent capacitance plate yarns do not touch.

Embodiments of the capacitive textile-sensor 90 according to the present invention can be utilized in a variety of applications. Some embodiments of a textile-sensor having a capacitive sensor according to the present invention are capable of measuring various physical, environmental, and/or physiological variables. For example, such a capacitive textile-sensor 90 can measure: (1) linear displacement; (2) strain caused by tensile or compressive force; (3) humidity; (4) change in circumference of a thoracic cavity, and hence respiration volume; (4) fetal movement; (5) flow and rate of a liquid, for example, perspiration rates in athletes. Such variables can be advantageously measured non-invasively and in real time.

In some embodiments, the capacitive textile-sensor 90 can be utilized in remote or ambulatory patient monitoring. In certain embodiments, the capacitive textile-sensor 90 may be incorporated into a garment and connected to a monitoring device. The garment can be in the form of a vest, for example. Such a textile-sensor garment enables real-time ambulatory monitoring, thus reducing the need for more costly, inconvenient, and possibly less effective in-house monitoring. And, because sensors are integrated into the garment, the sensors are not disruptive and are comfortable to wear. Since such a capacitive textile-sensor garment can be used for real-time ambulatory monitoring of lung function, it is a desirable alternative to conventional spirometry-based methods of respiratory monitoring. Such a wearable garment having integrated sensors is particularly useful for monitoring respiratory activity in patients with chronic obstructive pulmonary disease or cystic fibrosis. In addition, such a capacitive textile-sensor garment can be utilized to monitor respiratory patterns of a patient overnight, both in a clinic and remotely, to help diagnose obstructive sleep disorders, for example.

In another patient-related application, some embodiments of the capacitive textile-sensor 90 can be utilized to measure strain in continuous positive airway pressure (CPAP) mask attachment bands. By integrating the capacitive textile-sensor 90 in the attachment band and connecting the sensor to an alarm device, a user can be alerted when excessive force is being used to secure a CPAP mask, thereby helping the user avoid development of skin lesions due to repeated and/or excessive force from the band.

In some embodiments, the capacitive textile-sensor 90 can be integrated into a geotextile material for detection of geological forces. For example, a geotextile comprising the capacitive textile-sensor 90 can be utilized to measure the structural impact of seismic and climatic events on subsurface infrastructure, such as pipes, gas lines, and communications lines. This kind of monitoring capability would enable more informed post-natural disaster decision-making without the danger and cost of manually inspecting the damaged infrastructure. Some embodiments of such a capacitive textile-sensor geotextile can be utilized to generate data useful in designing disaster-proofing measures in terrain susceptible to movements such as avalanches and landslides. Likewise, such a capacitive textile-sensor geotextile can provide a means of measuring stability of land and predicting erosion events following a geological movement.

In another aspect of the present invention, embodiments of the electrically conductive textile sensor comprise a capability to auto-calibrate. When an electrically conductive textile sensor is placed in operation for a sensing activity, the MER, or level of resistance, can fluctuate as the textile in which the sensor is embedded is applied and as the sensor adjusts to and settles on the surface to which it is applied. Thus, it is important to understand the variation in sensor resistance during the period immediately following application and whether variation in resistance will stabilize sufficiently to allow accurate sensing. In sensors in which variation in resistance can be stabilized, it is important to estimate the amount of time needed to allow a stable baseline resistance to be established, that is, for the sensor to calibrate.

Experiment H

Resistance was measured over time in a textile-sensor sample under simulated wear conditions to determine whether resistance would calibrate to a baseline and, if so, the length of time for calibration to occur. The textile-sensor sample comprised an electrically conductive yarn and a stitch pattern comprising single jersey stitches 10, miss stitches 34, and tuck stitches 36 adaptable as a textile sensor. The textile-sensor sample was applied to a tubular form simulating either the calf or the ankle of a person's leg. The textile-sensor sample was placed on five different tubular forms for each of the calf simulations and for each of the ankle simulations. The five calf tubular forms had diameters of 8.6 inches, 9.4 inches, 10.2 inches, 11 inches, and 12.6 inches. The five ankle tubular forms also had diameters of 8.6 inches, 9.4 inches, 10.2 inches, 11 inches, and 12.6 inches. Measurements of resistance were taken beginning at time zero when the textile-sensor was initially applied to a form and in five second increments for a two minute period, providing 25 sample measurements for each location and diameter. Measurements were made using a Fluke 289 True RMS multimeter.

Figure 24:
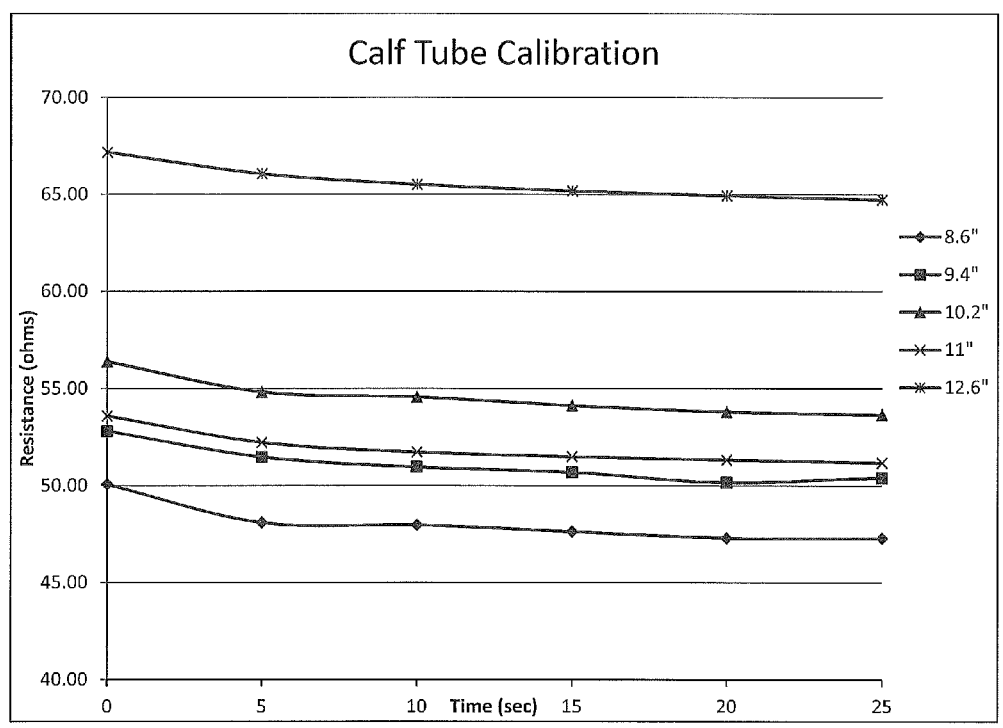
FIG. 24 is a plot graph of resistance measurements for the first six time increments shown in FIG. 23 for each diameter of a tube simulating the calf of a person's leg.
Figure 27:
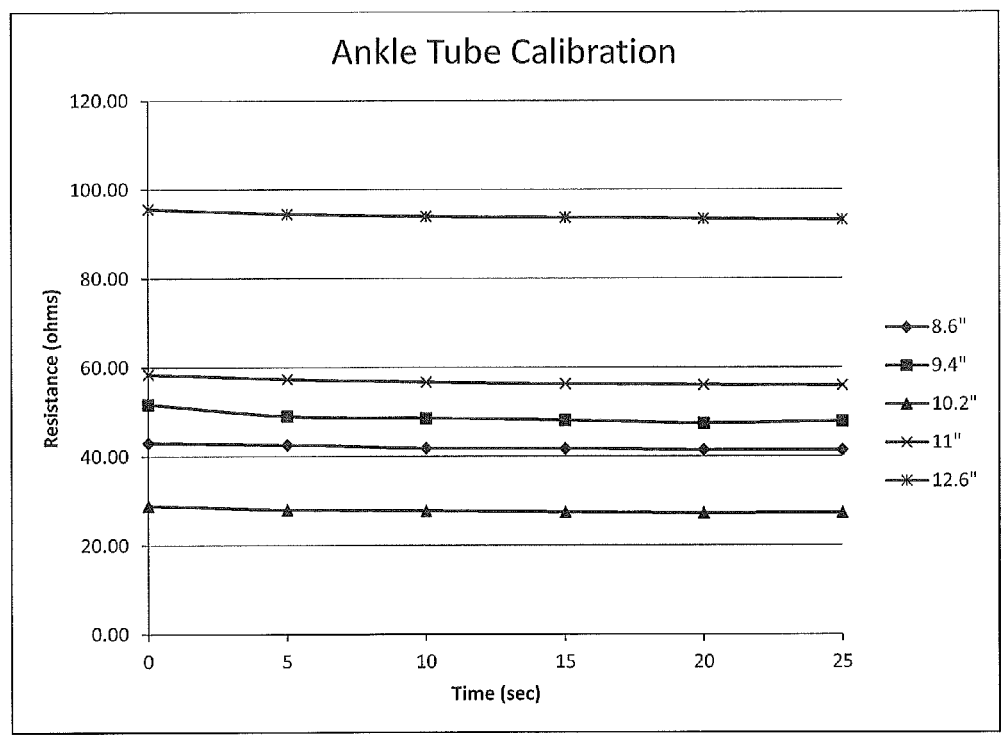
FIG. 27 is a plot graph of resistance measurements for the first six time increments shown in FIG. 25 for each diameter of a tube simulating the ankle of a person's leg.

The results of measurements of resistance for the textile-sensor on five diameters of a tube simulating the calf of a person's leg in five second increments after the textile-sensor is applied are shown in FIG. 23. The first six time measurements for each diameter tube for the calf simulation are shown graphically in FIG. 24. The percent change in resistance between each measurement after initial application for each diameter tube for the calf simulation is shown graphically in FIG. 25. The results of measurements of resistance for the textile-sensor on five diameters of a tube simulating the ankle of a person's leg in five second increments after the textile-sensor is applied are shown in FIG. 26. The first six time measurements for each diameter tube for the ankle simulation are shown graphically in FIG. 27. The percent change in resistance between each measurement after initial application for each diameter tube for the ankle simulation is shown graphically in FIG. 28.

As shown in FIG. 23 for the calf simulation, for the 8.6 inch diameter tube, the mean resistance of timed measurements is 47.14 ohms. The standard deviation of the sample mean is 0.72, and, assuming a normal distribution, at a 95% confidence level, the confidence interval (within which the true value of calibrated resistance is expected to occur) is 0.28. That is, there is a 95% probability that the mean from any calibration sample will be within ±0.28 ohms of a resistance of 47.14 ohms (or in the range of 46.86-47.42 ohms). The range of resistance in which true calibration is expected to occur was then correlated to the elapsed times for those levels of resistance after the textile-sensor sample was applied to the simulator tube. As shown in FIG. 23, calibration of resistance is expected to occur between 20-70 seconds (at a 95% confidence level) after the textile-sensor sample is applied.

For each of the different diameters of calf simulation tubes, mean resistance, standard deviation, confidence interval, and range for expected resistance calibration were determined, as shown in FIG. 23. The range of resistance in which true calibration is expected to occur was then correlated to the elapsed times for those levels of resistance after the textile-sensor sample was applied to each of the simulator tubes. Thus, at a 95% confidence level, calibration of resistance is expected to occur: for the 9.4 inch calf tube, between 30-85 seconds; for the 10.2 inch tube, between 25-65 seconds; for the 11 inch tube, between 25-70 seconds; and for the 12.6 inch tube between 30-65 seconds after the textile sample is applied. Across all five of the simulated calf diameters, calibration of resistance is expected to occur between 20-85 seconds after the textile-sensor sample is applied.

Figure 25:
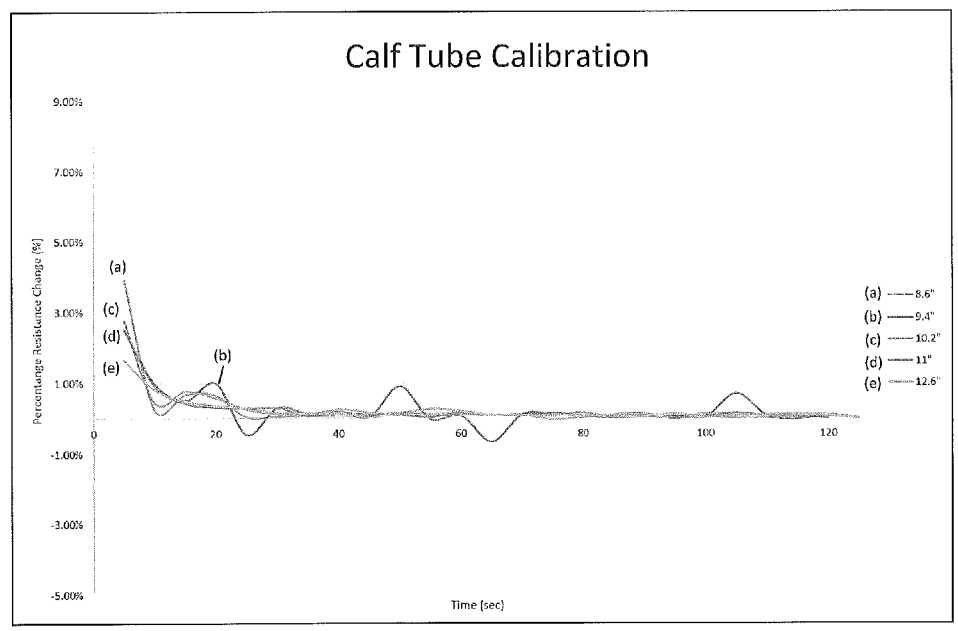
FIG. 25 is a plot graph of the percent change in resistance between each measurement after initial application shown in FIG. 23 for each diameter of a tube simulating the calf of a person's leg.

As shown in FIG. 25 for the calf simulation, the change in resistance between measurements for each diameter tube varied less than about 1.5% after the textile-sensor had been applied for 10 seconds, and was negligible after about 30 seconds. Accordingly, resistance in the textile-sensor is expected to calibrate to a relatively stable and defined resistance level in less than about 30 seconds.

As shown in FIG. 26 for the ankle simulation, for the 8.6 inch diameter tube, the mean resistance of timed measurements is 41.25 ohms. The standard deviation of the sample mean is 0.53, and, assuming a normal distribution, at a 95% confidence level, the confidence interval is 0.21. That is, there is a 95% probability that the mean from any calibration sample will be within ±0.21 ohms of a resistance of 41.25 ohms (or in the range of 41.04-41.46 ohms). The range of resistance in which true calibration is expected to occur was then correlated to the elapsed times for those levels of resistance after the textile-sensor sample was applied to the simulator tube. As shown in FIG. 26, calibration of resistance is expected to occur between 20-70 seconds (at a 95% confidence level) after the textile-sensor sample is applied.

For each of the different diameters of ankle simulation tubes, mean resistance, standard deviation, confidence interval, and range for expected resistance calibration were determined, as shown in FIG. 26. The range of resistance in which true calibration is expected to occur was then correlated to the elapsed times for those levels of resistance after the textile-sensor sample was applied to each of the simulator tubes. Thus, at a 95% confidence level, calibration of resistance is expected to occur: for the 9.4 inch ankle tube, between 20-80 seconds; for the 10.2 inch tube, between 20-70 seconds; for the 11 inch tube, between 30-60 seconds; and for the 12.6 inch tube between 30-65 seconds after the textile-sensor sample is applied. Across all five of the simulated ankle diameters, calibration of resistance is expected to occur between 20-80 seconds after the textile-sensor sample is applied.

Figure 28:
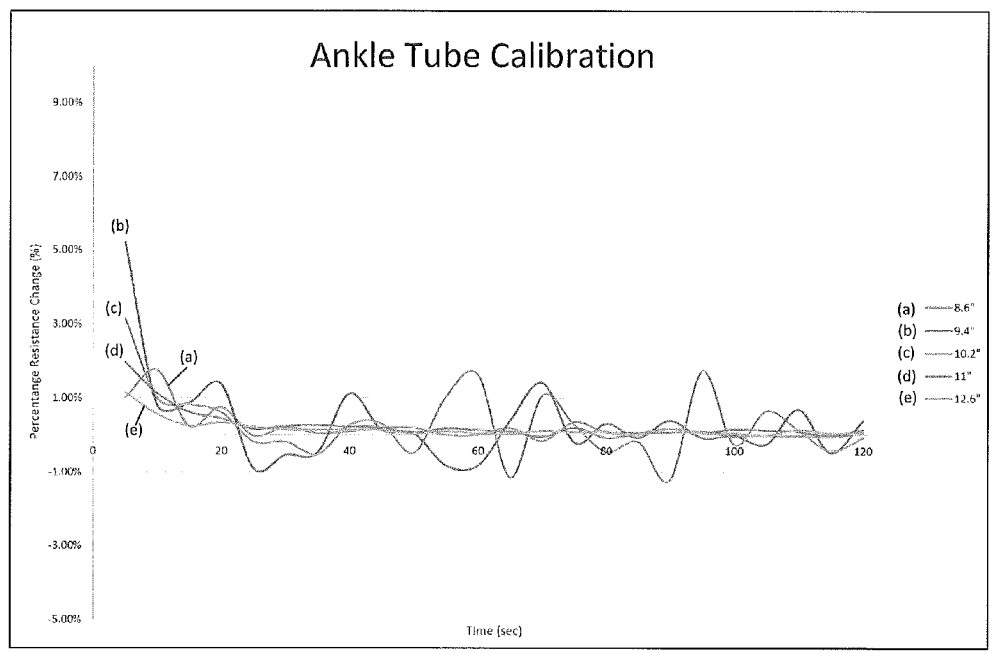
FIG. 28 is a plot graph of the percent change in resistance between each measurement after initial application shown in FIG. 26 for each diameter of a tube simulating the ankle of a person's leg.

As shown in FIG. 28 for the ankle simulation, the change in resistance between measurements for each diameter tube varied less than about 2% after the textile-sensor had been applied for 10 seconds, and was negligible after about 30 seconds. Accordingly, resistance in the textile-sensor is expected to calibrate to a relatively stable and defined resistance level in less than about 30 seconds.

Therefore, in some embodiments of the present invention, a textile can comprise a sensing area comprising an electrically conductive yarn knitted in the textile in which the sensing area comprises a combination of single jersey stitches 10, miss stitches 34, and/or tuck stitches 36, and the proportion of single jersey stitches 10, miss stitches 34, and/or tuck stitches 36 can be selected so as to provide a controlled amount of contact resistance in the textile. In such embodiments, the proportion of stitches selected provides a stitch structure that is sufficiently flexible and pliable to form over an organic shape or body, such as a person's limb, for example, over a calf or ankle. As illustrated in FIGS. 23-28, the pliable, form-fitting nature of such a textile-sensor is capable of automatically calibrating to a stable level of resistance within a short, definable, and reliably consistent time period across different sizes of limbs after being applied. This auto-calibration capability allows both standardization of the length of time to establish calibration and a calibrated resistance level to be incorporated as a baseline by electronics interfaced with the sensor.

Accordingly, in some embodiments, resistance in the textile-sensor can automatically calibrate to a stable baseline level after the textile sensor is applied to a body. For example, resistance in the textile-sensor can automatically calibrate to a stable baseline level within 90 seconds after the textile-sensor is applied to a person's leg. In particular, resistance in the textile-sensor can automatically calibrate to a stable baseline level between 20-85 seconds after the textile sensor is applied to a person's calf or ankle. The calibration level for resistance in a particular textile-sensor depends on the sensing activity for which the sensor is designed and the stitch structure selected for that sensing activity.

Some embodiments of the capacitive textile-sensor 90 can be utilized in other applications, including, for example, those related to: aged care, cardiovascular monitoring, home fetal monitoring, infant respiratory monitoring, mobile wellness, prosthetic touch, diabetic ulcer diagnosis, injury/stroke rehabilitation, workers in high risk environments, and clinical research.

Embodiments of a method for optimizing contact resistance in electrically conductive yarns and textiles, and textiles having such optimized contact resistance, of the present invention can comprise selecting a sensing activity for the textile; selecting a combination of variables from the group consisting of yarn variables, stitch variables, and textile variables; and knitting an electrically conductive yarn in the textile in accordance with the selected combination of variables, wherein the knitted combination of variables provides an optimal contact resistance in the textile correlated with a desired electrical conductivity for the sensing activity. In some embodiments, the knitted combination of variables provides a predictable yarn contact area (52) for the electrically conductive yarn correlated with the optimal contact resistance. In some embodiments, the yarn contact area (52) comprises a size and a shape, and the knitted combination of variables provides a predictable number and quality of yarn contact points (42, 44, 46, 48, 50) associated with the size and shape of the yarn contact area (52).

The combination of variables can be selected from yarn variables, including yarn type, yarn fabrication method, and yarn count. The combination of variables can be selected from stitch variables including stitch pattern, stitch length, and stitch percentage. The combination of variables can be selected from textile variables including electrical resistivity, fabric thickness, fabric weight, optical porosity, and percentage permanent stretch. In some embodiments, the stitch variables including stitch pattern can be selected from miss stitches 34, tuck stitches 36, and jersey stitches 10. Some embodiments can further include selecting a measurement sensitivity for the sensing activity, and the knitted combination of variables can provide the optimal contact resistance in the textile correlated with a desired electrical conductivity for the measurement sensitivity. In certain embodiments, selecting a sensing activity for the textile can further include selecting a plurality of different sensing activities for the textile. In various embodiments, the sensing activity can be selected from sensing tensile force, compressive force, movement, temperature, and physiological activity.

Other embodiments of a method for optimizing contact resistance in electrically conductive yarns and textiles, and textiles having such optimized contact resistance, can comprise selecting a combination of variables from the group consisting of yarn variables, stitch variables, and textile variables; and knitting an electrically conductive yarn having a yarn contact area in the textile in accordance with the selected combination of variables, wherein the knitted combination of variables provides a controllable amount of contact resistance in the textile. Some embodiments can further include selecting a sensing activity for the textile, and a controlled amount of contact resistance in the textile is correlated with a desired electrical conductivity for the sensing activity. In such an embodiment, the combination of variables can be selected from yarn variables including yarn type, yarn fabrication method, and yarn count. The combination of variables can be selected from stitch variables including stitch pattern, stitch length, and stitch percentage. The combination of variables can be selected from textile variables including electrical resistivity, fabric thickness, fabric weight, optical porosity, and percentage permanent stretch. In some embodiments, the stitch variables including stitch pattern can be selected from miss stitches 34, tuck stitches 36, and jersey stitches 10.

Some embodiments can further include increasing the size of the yarn contact area (52) to decrease the contact resistance. The yarn contact area (52) comprises a number and size of yarn contact points (42, 44, 46, 48, 50). Some embodiments can further include selecting an increased stitch length 20 to increase the number and size of yarn contact points (42, 44, 46, 48, 50) and the size of the yarn contact area (52), thereby decreasing the amount of contact resistance. Other embodiments can further include selecting stitch percentage of the miss stitches 34, tuck stitches 36, and jersey stitches 10 to control the number and size of yarn contact points (42, 44, 46, 48, 50) and the size of the yarn contact area (52), and thereby control the amount of contact resistance. Still other embodiments can further include selecting yarn type from the group consisting of filament yarn and staple fiber yarn to control the number and size of yarn contact points (42, 44, 46, 48, 50) and the size of the yarn contact area (52), and thereby control the amount of contact resistance. In such embodiments, yarn type can be selected from natural yarn and synthetic yarn. Still other embodiments can further include selecting an increased yarn count to increase the number and size of yarn contact points (42, 44, 46, 48, 50) and the size of the yarn contact area (52), thereby decreasing the amount of contact resistance.

Some embodiments can further include selecting an increased fabric thickness to increase the size of the yarn contact area (52), thereby decreasing the amount of contact resistance. Some embodiments can further include selecting an increased stitch percentage of miss stitches 34 and tuck stitches 36. Other embodiments can further include selecting an increased fabric weight to increase the size of the yarn contact area (52), thereby decreasing the amount of contact resistance. In such an embodiment, selecting an increased fabric weight can further include selecting an increased stitch percentage of miss stitches 34 and tuck stitches 36. Other embodiments can further include selecting a decreased optical porosity to increase the size of the yarn contact area (52), thereby decreasing the amount of contact resistance. In such an embodiment, selecting a decreased optical porosity can further include selecting an increased stitch percentage of tuck stitches 36. Still other embodiments can further include selecting a decreased percentage permanent stretch to increase the size of the yarn contact area (52), thereby decreasing the amount of contact resistance.

In some embodiments, the electrically conductive yarn in the textile can further include a resting mean electrical resistivity (MER) in the textile, and stitch percentage of the miss stitches 34, tuck stitches 36, and jersey stitches 10 can be selected to decrease the resting MER and the amount of contact resistance.

Some embodiments can further include selecting a measurement sensitivity for the sensing activity, and a controlled amount of contact resistance in the textile can be correlated with a desired electrical conductivity for the measurement sensitivity. In some embodiments, a measurement sensitivity can be selected from the group consisting of tensile force, compressive force, movement, temperature, and physiological activity. In some embodiments, the electrically conductive yarn in the textile can further include a mean electrical resistivity (MER), and stitch percentage of the miss stitches 34, tuck stitches 36, and jersey stitches 10 can be selected to provide a particular dynamic range in MER to control the measurement sensitivity during deformation of the textile. In particular, the dynamic range in MER can comprise a large dynamic range in MER to optimize the contact resistance for decreased measurement sensitivity for reliable measurements of compressive force over a large force range. Alternatively, the dynamic range in MER can comprise a small dynamic range in MER to optimize the contact resistance for increased measurement sensitivity for reliable measurements of compressive force over a small force range.

In some embodiments, the electrically conductive yarn in the textile can further include a mean electrical resistivity (MER), and stitch percentage of the miss stitches 34, tuck stitches 36, and jersey stitches 10 can be selected to provide a narrow range of MER variation to optimize the contact resistance for increased measurement sensitivity for reliable measurements of light weight pressures. In other embodiments, the electrically conductive yarn in the textile can further include an optical porosity, and a particular optical porosity can be selected to optimize the contact resistance to control the measurement sensitivity for compressive or tensile force loads. In particular, the optical porosity can comprise a low optical porosity to decrease the contact resistance for increased measurement sensitivity. Alternatively, the optical porosity can comprise a high optical porosity to increase the contact resistance for decreased measurement sensitivity. In some embodiments, stitch percentage of the miss stitches 34, tuck stitches 36, and jersey stitches 10 can be selected to optimize the amount of contact resistance to control temperature measurement sensitivity.

In certain embodiments of such a method, selecting a sensing activity for the textile can further include selecting a plurality of different sensing activities for the textile. In various such embodiments, the sensing activity can be selected from sensing tensile force, compressive force, movement, temperature, and physiological activity.

Some embodiments of a textile according to the present invention can comprise a sensing area comprising an electrically conductive yarn knitted in the textile and adapted for a sensing activity; and the sensing area comprising a combination of variables selected from the group consisting of yarn variables, stitch variables, and textile variables, wherein the combination of variables provides an optimal contact resistance in the textile correlated with a desired electrical conductivity for the sensing activity. In some embodiments, the combination of variables can comprise a predictable yarn contact area (52) for the electrically conductive yarn correlated with the optimal contact resistance. In some embodiments, the yarn contact area (52) can further include a size and a shape, and the combination of variables can further include a predictable number and quality of yarn contact points (42, 44, 46, 48, 50) associated with the size and shape of the yarn contact area (52).

The combination of variables can be selected from the group consisting of yarn type, yarn fabrication method, and yarn count. In some embodiments of such a textile, the combination of variables can be selected from the group consisting of stitch pattern, stitch length, and stitch percentage. In some embodiments of such a textile, the combination of variables can be selected from the group consisting of electrical resistivity, fabric thickness, fabric weight, optical porosity, and percentage permanent stretch. The stitch variables comprising stitch pattern can be selected from the group consisting of miss stitches 34, tuck stitches 36, and jersey stitches 10.

In some embodiments of such a textile, the sensing activity can comprise a measurement sensitivity, and the combination of variables comprises the optimal contact resistance in the textile correlated with a desired electrical conductivity for the measurement sensitivity. Some embodiments of such a textile can further include a plurality of sensing areas, and each of the sensing areas can be adapted for a different sensing activity. In some embodiments of such a textile, the sensing activity can be selected from sensing tensile force, compressive force, movement, temperature, and physiological activity.

Some embodiments of a textile according to the present invention can comprise a sensing area comprising an electrically conductive yarn knitted in the textile; and the sensing area comprising a combination of variables selected from the group consisting of yarn variables, stitch variables, and textile variables, wherein the combination of variables provides a controllable amount of contact resistance in the textile. The sensing area can be adapted for a sensing activity, and a controlled amount of contact resistance in the textile can be correlated with a desired electrical conductivity for the sensing activity. In some embodiments, the combination of variables can be selected from the group consisting of yarn type, yarn fabrication method, and yarn count. In some embodiments, the combination of variables can be selected from the group consisting of stitch pattern, stitch length, and stitch percentage. In some embodiments, the combination of variables can be selected from the group consisting of electrical resistivity, fabric thickness, fabric weight, optical porosity, and percentage permanent stretch. The stitch variables comprising stitch pattern can be selected from the group consisting of miss stitches 34, tuck stitches 36, and jersey stitches 10.

In some embodiments of the textile, the sensing activity can comprise a measurement sensitivity, and the combination of variables can comprise the optimal contact resistance in the textile correlated with a desired electrical conductivity for the measurement sensitivity. Some embodiments of the textile can further include a plurality of sensing areas, and each of the sensing areas can be adapted for a different sensing activity. In some embodiments of such a textile, the sensing activity can be selected from sensing tensile force, compressive force, movement, temperature, and physiological activity.

Some embodiments of a textile according to the present invention can comprise a method for making a textile sensor, comprising selecting a combination of variables from the group consisting of yarn variables, stitch variables, and textile variables; and knitting an electrically conductive yarn in the textile sensor in accordance with the selected combination of variables,
wherein the combination of variables is selected so as to provide a controlled amount of contact resistance in the textile sensor. Some embodiments of a textile according to the present invention can comprise a textile sensor, comprising an electrically conductive yarn knitted in the textile sensor in accordance with a combination of variables selected from the group consisting of yarn variables, stitch variables, and textile variables, wherein the combination of variables is selected so as to provide a controlled amount of contact resistance in the textile sensor.

In some such embodiments, the selected combination of variables can further comprise an increased tex yarn count so as to provide an increased cover factor and a decreased amount of contact resistance. In some such embodiments, the selected combination of variables can further comprise a filament yarn so as to provide an increased amount of contact resistance, whereby the textile sensor is adapted to have decreased measurement sensitivity for measuring large mass or pressure differences. In some such embodiments, the selected combination of variables can further comprise a staple fiber yarn so as to provide a decreased amount of contact resistance,
whereby the textile sensor is adapted to have increased measurement sensitivity for measuring small mass or pressure differences.

Some such embodiments can further comprise a capacitive textile-sensor 90 having at least two integrally knit capacitor plate elements 92 comprising the electrically conductive yarn and having a configuration adapted for a sensing activity. In such a capacitive textile-sensor 90, the configuration can further comprise a selected contact resistance within the knitted capacitor plate elements 92. In such a capacitive textile-sensor 90, the capacitor plate elements 92 can each further comprise a defined yarn contact area (52), and the selected contact resistance can comprise a selected number and shape of yarn contact points (42, 44, 46, 48, 50) within each yarn contact area (52). In such a capacitive textile-sensor 90, the configuration can further comprise a selected size, shape, and position of the capacitor plate elements 92 and a diaelectric material within the capacitive textile-sensor 90. In such a capacitive textile-sensor 90, a measure of capacitance by the capacitive textile-sensor 90 can correlate with an amount of strain in the capacitive textile-sensor 90. In such a capacitive textile-sensor 90, the capacitor plate elements 92 can be knit as a series of spaced apart, interdigitated fingers. In such a capacitive textile-sensor 90, the capacitor plate elements 92 can be knit into a defined area of two opposable fabric layers. In such a capacitive textile-sensor 90, the capacitive textile-sensor 90 can be knit in a wearable garment during fabrication of the garment.

In some embodiments of a textile sensor according to the present invention, resistance in the textile sensor can automatically calibrate to a stable baseline level after the textile sensor is applied to a body. In some embodiments, resistance in the textile sensor can automatically calibrate to a stable baseline level within 90 seconds after the textile sensor is applied to a person's leg. In some embodiments, resistance in the textile sensor can automatically calibrate to a stable baseline level between 20-85 seconds after the textile sensor is applied to a person's calf or ankle.

A method for optimizing contact resistance in electrically conductive yarns and textiles and textiles having such optimized contact resistance according to the present invention provide advantages over conventional approaches to construct electrically conductive yarns and textiles. One advantage is that embodiments of the present invention comprise a method for designing a textile structure to optimize the position and size of yarn contact areas (52) that allows control of electrical contact resistance and thus sensitivity of the textile structure. Thus, such a method provides a basis for varying a textile structure for specific applications. As a result, such a method can be utilized in a wide variety of applications and products.

Another advantage is that embodiments of the present invention utilize predictable characteristics and variables of yarns and textiles that improve control of contact resistance. Accordingly, embodiments of the present invention provide for optimization of contact resistance in electrically conductive yarns in a simple, cost-effective, and repeatable manner.

Another advantage is that embodiments of the present invention allow use of a single electrically conductive fiber type in a textile sensor.

Another advantage is that embodiments of a "textile-sensor" of the present invention provide the capability integrated into a textile to monitor a plurality of point outputs (such as physiological variables), thus allowing a more comprehensive and/or averaged measurement of such outputs.

Another advantage is that embodiments of the present invention allow a textile structure having optimized contact resistance to be utilized as a sensor for force, pressure, movement, temperature, and/or physiological activity.

Another advantage is that embodiments of the present invention thus providing enhanced sensing capabilities of such fabrics can be incorporated into composite structures. Such combination sensors can provide either passive or active sensing platforms. In one application, such sensors can be utilized to remotely measure physiological output of the human body. A variety of data obtainable utilizing such fabrics can be used, for example, to improve health outcomes, to enhance safety among athletes, first responders, and soldiers, and for industrial applications.

Another advantage is that embodiments of the present invention comprising knitted fabrics can provide superior draping characteristics (ability to form on organic shapes) over woven materials, thereby enhancing user comfort, durability, and cost.

In addition, some embodiments of the present invention provide advantages in manufacturing over conventional textile-based sensors. For example, such a method can be implemented using computer aided design (CAD) programming prior to manufacture, thereby preventing wasted labor, machinery, and materials costs for trial and error construction. A CAD system programmed for manufacturing a textile structure having optimizing contact resistance can be used to create such a textile structure when the flexible conducting network of electrically conductive yarn is at rest or when subjected to tension or compression. Stitch and yarn variables controllable for optimizing contact resistance in a textile structure can be implemented with CAD software usable in existing commercial knitting machines. Thus, embodiments of the present invention can provide the advantages of simplified design and manufacturing processes with significant reductions in costs as compared to existing textile sensors. By using existing commercial equipment, embodiments of the present invention can further provide the advantage of a means for repeatably producing a durable resistive textile-sensor.

Although the present invention has been described with reference to particular embodiments, it should be recognized that these embodiments are merely illustrative of the principles of the present invention. Those of ordinary skill in the art will appreciate that a method for optimizing contact resistance in electrically conductive yarns and textiles and yarns and textiles so optimized of the present invention may be constructed and implemented in other ways and embodiments. Accordingly, the description herein should not be read as limiting the present invention, as other embodiments also fall within the scope of the present invention.

What is claimed is:

1. A textile having at least one fully integrated knitted capacitive sensor, the textile comprising:
   at least one capacitive sensor comprising an electrically conductive yarn knitted in the textile, wherein the capacitive sensor is configured for measurement of at least one sensing activity selected from the group consisting of: linear displacement; at least one of tensile and compressive force; humidity; physiological activity; and geological activity;
   wherein the capacitive sensor comprises at least two integrally knitted capacitor plate elements comprising the electrically conductive yarn and a stitch pattern, the stitch pattern comprising jersey stitches and stitches selected from one or more of the group consisting of: miss stitches and tuck stitches;
   wherein the stitch pattern of the capacitor plate elements defines a contact area resulting from a number of contact points between stitches; and
   wherein changes in conductivity in the capacitive sensor due to changes in the contact area between stitches are measurable and permit monitoring of the sensing activity.

2. The textile sensor of claim 1, wherein the electrically conductive yarn comprises a filament yarn, and wherein the contact area is further defined by the filament yarn.

3. The textile sensor of claim 1, wherein the electrically conductive yarn comprises a staple fiber yarn, and wherein the contact area is further defined by the staple fiber yarn.

4. The textile sensor of claim 1, wherein the capacitive sensor further comprises a selected size, shape, and position of the capacitor plate elements.

5. The textile of claim 1, wherein the stitch pattern comprises 50% jersey stitches and the remainder of stitches selected from one or more of the group consisting of: miss stitches and tuck stitches.

6. The textile of claim 1, wherein a percentage of miss stitches in the stitch pattern in the capacitive sensor is at least 5% and at most 45%.

7. The textile of claim 1, wherein a percentage of tuck stitches in the stitch pattern in the capacitive sensor is at least 5% and at most 45%.

8. The textile of claim 1, wherein the capacitive sensor further comprises a selected size, shape, and position of and of a diaelectric material knitted within the capacitive sensor.

9. The textile of claim 1, wherein the textile further comprises an electrical resistivity, a fabric thickness, a fabric weight, an optical porosity, and a percentage permanent stretch, which further defines the contact area resulting from each contact point.

10. The textile of claim 1, wherein the sensing activity comprises a measurement sensitivity, and wherein the stitch pattern is selected such that the number of contact points between the stitches result in contact area that is correlated with the measurement sensitivity.

11. The textile of claim 1, wherein the sensing activity comprises sensing physiological activity, and wherein sensing physiological activity comprises an activity selected from a group consisting of the following: monitoring respiratory activity; diagnosing sleep disorders; cardiovascular monitoring; prosthetic touch applications; diabetic ulcer diagnosis; and monitoring fetal movement.

12. A geotextile material comprising the textile of claim 1, wherein the sensing activity comprises sensing geological activity.

13. A mask attachment band, comprising the textile of claim 1, wherein the sensing activity comprises measuring tensile force.

14. A material comprising the textile of claim 1, wherein the sensing activity comprises sensing structural movement.

15. A garment comprising the textile of claim 1, wherein the sensing activity comprises measuring perspiration.

* * * * *